US009133435B2

(12) United States Patent
Takahashi et al.

(10) Patent No.: US 9,133,435 B2
(45) Date of Patent: Sep. 15, 2015

(54) METHOD FOR INDUCTION/DIFFERENTIATION INTO PHOTORECEPTOR CELL

(75) Inventors: Masayo Takahashi, Kobe (JP); Fumitaka Osakada, Kobe (JP); Michiko Mandai, Kobe (JP); Hanako Ikeda, Kyoto (JP)

(73) Assignee: RIKEN, Wako (JP)

( * ) Notice: Subject to any disclaimer, the term of this patent is extended or adjusted under 35 U.S.C. 154(b) by 285 days.

(21) Appl. No.: 12/523,444

(22) PCT Filed: Jan. 11, 2008

(86) PCT No.: PCT/JP2008/050305
§ 371 (c)(1),
(2), (4) Date: Oct. 13, 2009

(87) PCT Pub. No.: WO2008/087917
PCT Pub. Date: Jul. 24, 2008

(65) Prior Publication Data
US 2010/0105137 A1    Apr. 29, 2010

(30) Foreign Application Priority Data
Jan. 18, 2007 (JP) ................................. 2007-009617

(51) Int. Cl.
*C12N 15/00* (2006.01)
*C12N 5/0793* (2010.01)
*C12N 5/079* (2010.01)
*C12N 5/0797* (2010.01)
*A61K 35/12* (2015.01)

(52) U.S. Cl.
CPC .............. *C12N 5/062* (2013.01); *C12N 5/0621* (2013.01); *C12N 5/0623* (2013.01); *A61K 35/12* (2013.01); *C12N 2500/33* (2013.01); *C12N 2500/99* (2013.01); *C12N 2501/113* (2013.01); *C12N 2501/115* (2013.01); *C12N 2501/16* (2013.01); *C12N 2501/385* (2013.01); *C12N 2501/415* (2013.01); *C12N 2501/999* (2013.01); *C12N 2506/02* (2013.01); *C12N 2506/08* (2013.01); *C12N 2533/00* (2013.01)

(58) Field of Classification Search
CPC .............. C12N 5/0621; C12N 5/0623; C12N 2506/02; C12N 5/06; C12N 5/0068; C12N 2566/08; C12N 2533/00
See application file for complete search history.

(56) References Cited

U.S. PATENT DOCUMENTS

| 7,541,186 B2 * | 6/2009 | Reh et al. ........................ 435/377 |
| 7,736,896 B2 | 6/2010 | Klimanskaya et al. |
| 2013/0224156 A1 | 8/2013 | Takahashi et al. |

FOREIGN PATENT DOCUMENTS

| EP | 1783205 A1 | 9/2007 |
| EP | 2128244 A1 | 12/2009 |
| WO | WO 2004/090110 | * 10/2004 |
| WO | WO 2005/123902 A1 | 12/2005 |
| WO | WO 2008/087917 A1 | 7/2008 |
| WO | WO 2009/051671 A1 | 4/2009 |

OTHER PUBLICATIONS

Livesey et al (Nature Reviews, Neuroscience, 2: 109-118, 2001).*
Yaron et al (Development, 133(7): 1367-78, 2006).*
Ueno et al (PNAS, 103(25): 9554-9559, 2006).*
Geling et al., *EMBO Reports*, 3(7): 688-694 (2002).
Hirano et al., *Developmental Dynamics*, 228: 664-671 (2003).
Kawasaki et al., *Proc. Natl. Acad. Sci. USA*, 99(3): 1580-1585 (Feb. 5, 2002).
Lamba et al., *Proc. Natl. Acad. Sci. USA*, 103(34): 12769-12774 (Aug. 22, 2006).
Mandai et al., *Koseirodosho Nanjisei Shikkan Kokufuku Kenkyu Jigyo Momaku Myakurakumaku, Shishinkei Ishukusho Chosa Kenkyuhan, Heisei 18 Nendo Hankaigi Program*, p. 70 (Jan. 12, 2007), English Language International Report on Patentability.
Ooto et al., *Investigative Ophthalmology & Visual Science*, 44(6): 2689-2693 (Jun. 2003).
Osakada et al., *Nature Biotechnology*, 26(2): 215-224 (Feb. 2008).
Ikeda et al., *Proc. Natl. Acad. Sci. U.S.A.*, 102(32): 11331-11336 (Aug. 9, 2005).
Watanabe et al., *Nature Neuroscience*, 8(3): 288-296 (Mar. 2005).
Igaku-no-Ayumi, 220(2): 143-146 (2007).
Young et al., *Neuron*, 41: 867-879 (2004).
Japanese Patent Office, Office Action in Japanese Patent Application No. 2008-554025 (Dec. 4, 2013).
Weihofen et al., *J. Biol. Chem.*, 278(19): 16528-16533 (2003).
Japanese Patent Office, Office Action in Japanese Patent Application No. 2008-554025 (Sep. 17, 2013).
Fusaki et al., *Proc. Jpn. Acad., Ser. B*, 85(8): 348-362 (2009).
Maminishkis et al., *Invest. Ophthalmol. Vis. Sci.*, 47(8): 3612-3624 (2006).
Okita et al., *Nature Methods*, 8(5): 409-412 (2011) (with "Online Methods," 2 pgs.).
Osakada et al., *J. Cell Sci.*, 122(17): 3169-3179 (2009).

(Continued)

*Primary Examiner* — Deborah Crouch
*Assistant Examiner* — Magdalene Sgagias
(74) *Attorney, Agent, or Firm* — Leydig, Voit & Mayer, Ltd.

(57) ABSTRACT

The present invention provides a method of producing primate retinal progenitor cells, comprising culturing primate embryonic stem cells as suspended aggregates in a serum-free medium, and obtaining retinal progenitor cells from the culture. The present invention further provides a method of producing photoreceptor precursor cells, comprising culturing isolated retinal progenitor cells differentiated from embryonic stem cells, under adhesive conditions, in the presence of a gamma secretase inhibitor, and obtaining a photoreceptor precursor from the culture.

26 Claims, 9 Drawing Sheets

(56) References Cited

OTHER PUBLICATIONS

Japanese Patent Office, Office Action in Japanese Patent Application No. 2008-554025 (Dec. 4, 2012).
European Patent Office, Supplementary European Search Report in European Patent Application No. 08703169.6 (Apr. 3, 2012).
Jadhav et al., *Development*, 133: 913-923 (Mar. 1, 2006).
Japanese Patent Office, International Search Report in International Patent Application No. PCT/JP2008/050305 (Apr. 22, 2008).
Nelson et al., *Developmental Neuroscience*, 28: 128-141 (Jan. 1, 2006).
Nelson et al., *Developmental Biology*, 304(2): 479-498 (Apr. 15, 2007).
International Bureau of WIPO, International Preliminary Report on Patentability in International Patent Application No. PCT/JP2008/050305 (Jul. 21, 2009).
Yaron et al., *Development*, 133: 1367-1378 (Apr. 1, 2006).
Chung et al., "Human Embryonic Stem Cell Lines Generated without Embryo Destruction," *Cell Stem Cell*, 2(2): 113-117 (Feb. 2008).
Eiraku et al., "Self-organizing optic-cup morphogenesis in three-dimensional culture," *Nature*, 472(7341): 51-56 (Apr. 7, 2011).
European Patent Office, Office Action in European Patent Application No. 08703169.6 (Nov. 18, 2013).

* cited by examiner

METHOD FOR INDUCTION/DIFFERENTIATION INTO PHOTORECEPTOR CELL

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,628 Byte ASCII (Text) file named "705215SequenceListing.TXT," created on Oct. 12, 2009.

TECHNICAL FIELD

The present invention relates to a method of producing retinal progenitor cells, photoreceptor precursors, photoreceptors and the like.

BACKGROUND ART

The number of patients suffering blindness due to a retinal degenerative disease such as age-related macular degeneration or retinitis pigmentosa has been increasing. Because a disorder of photoreceptors is the direct cause of blindness in these diseases, production of photoreceptors (or photoreceptor precursors) in vitro would possibly contribute significantly to research into these diseases and development of therapies for these diseases.

Including the present inventors, many groups have attempted to generate photoreceptors from iris tissue (non-patent documents 1, 2), ciliary tissue (non-patent document 3), or embryonic stem (ES) cells (non-patent documents 4-6). Compared with tissue stem cells, ES cells have the capability of proliferating infinitely and permit production of sufficient numbers of cells for research and treatment, and are therefore superior. Recent studies have demonstrated that retinal progenitor cells can be efficiently produced from ES cells in vitro. By contrast, the in vitro generation of photoreceptors from ES cell-derived progenitor cells remains inefficient unless the progenitor cells are co-cultured with developing retinal tissue. For example, in a previous report by the present inventors (non-patent document 6), the present inventors showed efficient induction (up to 16%) of neural retinal progenitor cells from mouse ES cells using a serum-free floating culture of embryoid body-like aggregates (SFEB) system combined with treatments with Dkk1, LeftyA, serum and Activin (SFEB/DLFA) (non-patent document 7). ES-derived neural retinal progenitor cells, when co-cultured with embryonic retinal tissue, are capable of producing photoreceptors. However, no method has been established for producing photoreceptors under culture conditions without the co-culture. In particular, a defined method of culture wherein photoreceptors are efficiently produced from human ES cell is expected to overcome the definitive limitation on transplantation therapy; there is demand for the development of the method.

In the document 7, the present inventors studied for effects of exogenous factors (Fgf, taurine, shh, and /RA) on SFEB/DLFA-treated cells without sorting, and were unable to find an evidently positive effect on the differentiation into rhodopsin+ photoreceptors. For induction of retinal progenitor cells from mouse embryonic stem cells, addition of FCS was essential.

non-patent document 1: Haruta, M. et al. Induction of photoreceptor-specific phenotypes in adult mammalian iris tissue. Nat. Neurosci. 4, 1163-1164 (2001).

non-patent document 2: Sun, G. et al. Retinal stem/progenitor properties of iris pigment epithelial cells. Dev. Biol. 289, 243-252 (2006).

non-patent document 3: Tropepe, V. et al. Retinal stem cells in the adult mammalian eye. Science 287, 2032-2036 (2000).

non-patent document 4: Zhao, X., Liu, J. & Ahmad, I.Differentiation of embryonic stem cells into retinal neurons. Biochem. Biophys. Res. Commun. 297, 177-184 (2002).

non-patent document 5: Hirano, M. et al. Generation of structures formed by lens and retinal cells differentiating from embryonic stem cells. Dev. Dyn. 228, 664-671 (2003).

non-patent document 6: Ikeda, H. et al. Generation of Rx+/Pax6+ neural retinal precursors from embryonic stem cells. Proc. Natl. Acad. Sci. USA 102, 11331-11336 (2005).

non-patent document 7: Watanabe, K. et al. Directed differentiation of telencephalic precursors from embryonic stem cells. Nat. Neurosci. 8, 288-296 (2005).

DISCLOSURE OF THE INVENTION

Problems to be Solved by the Invention

In view of the above-described circumstances, the present invention is directed to providing a method of efficiently producing retinal progenitor cells or photoreceptors from mammalian (particularly human) ES cells.

Means of Solving the Problems

The present inventors conducted extensive investigations with the aim of accomplishing the above-described object, and found that by treatment with a gamma secretase inhibitor (gamma secretase inhibitory drug), a $Crx^+$ photoreceptor precursors are efficiently induced in an aggregate culture of FACS-purified retinal progenitor cells ($Rx^+$ cells) derived from mouse ES cell. At the same time, these cells produced cone photoreceptors at high frequency, but the differentiation of $rhodopsin^+$ rod photoreceptors was not more efficient. However, further treatment with FGF, shh, taurine and/or retinoic acid significantly raised the frequency of $rhodopsin^+$ cells.

Furthermore, the present inventors also investigated a method of efficiently generating retinal progenitor cells and/or photoreceptors from primate (human, monkey) ES cells. By suspension culture without feeders and serum, but containing Wnt and Nodal inhibitors (SFEB/DL culture), differentiation from ES cells into Rx-positive retinal progenitor cells or Mitf-positive pigment epithelial cells having a characteristic morphology was induced. Under these conditions, differentiation from Rx-positive retinal progenitor cells to photoreceptors only rarely occurred; however, when the progenitor cells were further treated with retinoic acid and taurine, differentiation from ES cell-derived progenitor cells to rhodopsin-positive/Recoverin-positive photoreceptors was remarkably promoted.

Based on the findings shown above, the present invention has been developed.

Accordingly, the present invention relates to the following:

[1] A method of producing primate retinal progenitor cells, comprising culturing primate embryonic stem cells as suspended aggregates in a serum-free medium, and obtaining retinal progenitor cells from the culture.

[2] The method described in [1], wherein the cultivation of the suspended aggregates is performed in the serum-free medium over the entire period thereof.

[3] The method described in [1] or [2], wherein the serum-free medium contains at least any one inhibitor selected from the group consisting of a Nodal signal inhibitor and a Wnt signal inhibitor.

[4] The method described in [3], wherein the serum-free medium contains a Nodal signal inhibitor and a Wnt signal inhibitor.

[5] The method described in [3], wherein the Nodal signal inhibitor is Lefty-A or SB-431542.

[6] The method described in [3], wherein the Wnt signal inhibitor is Dkk1, CKI-7 or D4476.

[7] The method described in [1], wherein each aggregate at the start of cultivation is configured with 2 to 50 embryonic stem cells.

[8] The method described in [1], wherein the suspended aggregates are cultured for at least 3 days.

[9] The method described in [1], wherein the retinal progenitor cells are neural retinal progenitor cells or retinal pigment epithelium progenitor cells.

[10] The method described in [1], further comprising culturing the cultured cells under adhesive conditions after cultivation of the suspended aggregates.

[11] A method of producing primate retinal pigment epithelial cells, comprising culturing primate embryonic stem cells as suspended aggregates in a serum-free medium, further culturing the cultured cells under adhesive conditions, and obtaining retinal pigment epithelial cells from the culture.

[12] A method of producing primate photoreceptors or a precursor thereof, comprising culturing primate embryonic stem cells as suspended aggregates in a serum-free medium, further culturing the cultured cells under adhesive conditions, and obtaining photoreceptors or a precursor thereof from the culture.

[13] The method described in [12], wherein the cultivation under adhesive conditions is performed in a medium containing at least one factor selected from the group consisting of retinoic acid and taurine.

[14] The method described in [13], wherein the medium contains retinoic acid and taurine.

[15] The method described in [13], wherein at least one factor selected from the group consisting of retinoic acid and taurine is added to the culture under adhesive conditions at a stage after the emergence of photoreceptor precursors in the culture.

[16] A method of producing photoreceptor precursors, comprising culturing isolated retinal progenitor cells differentiated from embryonic stem cells under adhesive conditions in the presence of a gamma secretase inhibitor, and obtaining photoreceptor precursors from the culture.

[17] The method described in [16], wherein the gamma secretase inhibitor is DAPT.

[18] A method of producing cone photoreceptors, comprising culturing isolated retinal progenitor cells differentiated from embryonic stem cells under adhesive conditions in the presence of a gamma secretase inhibitor, and obtaining cone photoreceptors from the culture.

[19] The method described in [18], wherein the gamma secretase inhibitor is DAPT.

[20] A method of producing rod photoreceptors, comprising culturing isolated retinal progenitor cells differentiated from embryonic stem cells under adhesive conditions in the presence of a gamma secretase inhibitor, further culturing the cultured cells under adhesive conditions in the presence of at least any one factor selected from the group consisting of an FGF, an shh signal promoter, retinoic acid and taurine, and obtaining rod photoreceptors from the culture.

[21] The method described in [20], wherein the further cultivation is performed in the presence of a gamma secretase inhibitor.

[22] The method described in [21], wherein the gamma secretase inhibitor is DAPT [21].

Effect of the Invention

Use of a method of the present invention makes it possible to efficiently generate retinal progenitor cells or photoreceptors from ES cells without co-culture with retinal tissue. In particular, a method of the present invention is advantageous in that retinal progenitor cells or photoreceptors can be efficiently produced from primate ES cells under defined culture conditions.

The present invention can largely promote the development of transplantation therapies for retinal diseases based on human ES cells.

BEST MODE FOR CARRYING OUT THE INVENTION

Figure 1:
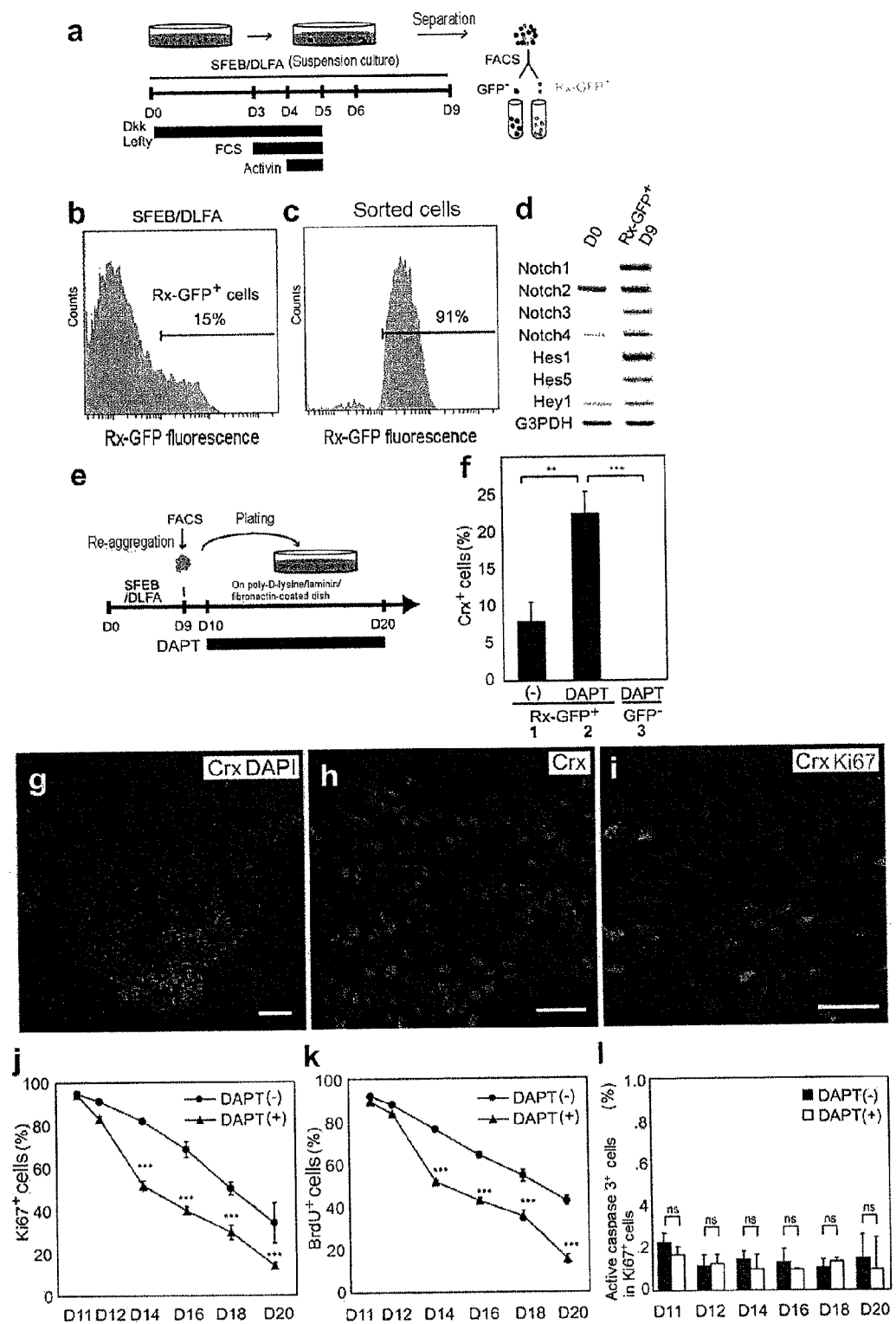
FIG. 1 Efficient generation of photoreceptor precursors from FACS-purified ES-derived neural retinal progenitor cells using a gamma secretase inhibitor. (a) A schematic diagram showing the procedure for the enrichment of $Rx^+$ retinal progenitor cells by FACS. D, number of culturing days. (b, c) Flow cytometry analysis. SFEB/DLFA-treated (day 9) (b), or sorted $Rx\text{-}GFP^+$ cells (c) were analyzed. The percentage of $Rx\text{-}GFP^+$ cells is shown. (d) RT-PCR analysis for genes involved in Notch signaling in sorted $Rx\text{-}GFP^+$ cells or undifferentiated (D0) cells. (e) A schematic diagram showing the procedure for differentiation of photoreceptor precursors from sorted $Rx\text{-}GFP^+$ cells. (f) $Rx\text{-}GFP^+$ cells were treated with or without DAPT, the $Rx\text{-}GFP^-$ cells were treated with DAPT from day 10, and on day 20 the percentage of $Crx^+$ cells was determined. , $P<0.01$, *, $P<0.001$, Tukey's test. (g-i) Immunohistological analyses of sorted $Rx\text{-}GFP^+$ cells treated with DAT, on day 20 (g, h) and on day 18 (i). (g, h) $Crx^+$ (red) cells were efficiently generated from the sorted cells. In g, the nuclei were counterstained with DAPI (blue). (i) $Crx^+$ (red) cells were negative for Ki67 (green). (j, k) Sorted cells were treated with DAPT (triangle) or not treated (circle), and the percentages of $Ki67^+$ (j) and $BrdU^+$ (k) cells on various days of differentiation were determined. ***, $P<0.001$, Bonferroni test. (l) At any number of days of differentiation, no difference was observed between the percentage of active caspase $3^+$ cells in a $Ki67^+$ population of the DAPT-treated and untreated cells on each differentiation day (ns, not significant, Bonferroni test). The scale bar is 100 μm long for "g" and 20 μm for h and i.

The present invention provides an improved method of producing retinal progenitor cells, photoreceptor precursors or photoreceptors from embryonic stem cells. Hereinafter, the present invention is described in detail.

(1. Embryonic Stem Cells)

"An embryonic stem cell (ES cell)" refers to a cell that can be cultured in vitro and possesses pluripotency for differentiation into all types of cells that constitute a living organism.

As embryonic stem cells, for example, cells derived from a warm-blooded animal, preferably a mammal, can be used. As examples of the mammal, primates such as humans and monkeys, rodents such as mice, rats, guinea pigs, and hamsters, rabbits, cats, dogs, sheep, pigs, bovines, horses, and goat can be mentioned.

Specifically, as examples of embryonic stem cells used in a method of the present invention, embryonic stem cells of a mammal or the like established by culturing a pre-implantation early embryo (hereinafter, abbreviated as "embryonic stem cells I"), embryonic stem cells established by culturing an early embryo prepared by nuclear-transplanting the nucleus of a somatic cell (hereinafter, abbreviated as "embryonic stem cells II"), and embryonic stem cells prepared by modifying a gene on the chromosome of embryonic stem cells I or II using a gene engineering technique (hereinafter, abbreviated as "embryonic stem cells III") can be mentioned.

More specifically, as embryonic stem cells I, embryonic stem cells established from an inner cell mass that constitutes an early embryo, EG cells established from a primordial germ cell, cells isolated from a cell population possessing the pluripotency of pre-implantation early embryos (for example, primordial ectoderm), or cells obtained by culturing these cells and the like can be mentioned.

Embryonic stem cells I can be prepared by culturing a pre-implantation early embryo according to a method described in the literature (Manipulating the Mouse Embryo A Laboratory Manual, Second Edition, Cold Spring Harbor Laboratory Press (1994)).

Embryonic stem cells II can be prepared using methods reported by Wilmut et al. (Nature, 385, 810 (1997)), Cibelli et al. (Science, 280, 1256 (1998)), Akira Iritani et al. (Protein, Nucleic Acid and Enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)) and others, for example, as described below.

By extracting the nucleus of a mammalian cell and then reprogramming the nucleus (an operation to return the nucleus to a state to resume development), initiating development using a method wherein the nucleus is injected into an enucleated mammalian unfertilized egg, and culturing the egg that has started development, an egg that has the nucleus of another somatic cell, and has begun normal development, is obtained.

For reprogramming the nucleus of a somatic cell, a plurality of methods are known. For example, the nucleus can be reprogrammed by changing the medium being used to culture the nucleus donor cell from a medium containing 5 to 30%, preferably 10%, of fetal calf serum (for example, M2 medium), to an oligotrophic medium containing 0 to 1%, more preferably 0.5%, of fetal calf serum, and culturing the cell for 3 to 10% days, preferably 5 days, to induce the cell cycle into a resting phase state (G0 stage or G1 stage).

The nucleus can also be reprogrammed by injecting the nucleus of the nucleus donor cell into an enucleated unfertilized egg of a mammal of the same species, and culturing the cell for several hours, preferably about 1 to 6 hours.

The reprogrammed nucleus is able to begin development in the enucleated unfertilized egg. As methods of allowing a reprogrammed nucleus to begin development in an enucleated unfertilized egg, a plurality of methods are known. By transplanting a nucleus reprogrammed by inducing the cell cycle to a resting phase state (phase G0 or phase G1), into an enucleated unfertilized egg of a mammal of the same species by the electrofusion method and the like, the egg can be activated and allowed to begin development.

A nucleus reprogrammed by injecting the nucleus into an enucleated unfertilized egg of a mammal of the same species is transplanted back to an enucleated unfertilized egg of a mammal of the same species by a method using a micromanipulator or the like, and stimulated with an egg activator (for example, strontium and the like), and thereafter treated with an inhibitor of cell division (for example, cytocalacin B and the like) to suppress the release of the second polar body, whereby development can be initiated. This method is suitable when the mammal is, for example, a mouse or the like.

Provided that an egg that once began to develop is obtained, embryonic stem cells can be acquired using publicly known methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8% Gene Targeting, Preparation of Mutant Mice Using ES Cells, Yodosha (1995) and the like.

Embryonic stem cells III can be prepared by, for example, homologous recombination technology. As examples of the gene on the chromosome to be modified in preparing embryonic stem cells III, histocompatibility antigen genes, genes related to diseases based on retinal cell disorders and the like can be mentioned. By knocking in a labeling gene (for example, a fluorescent protein such as GFP) into a gene that encodes a differentiation marker of retinal progenitor cell or photoreceptor precursor (for example, Rx) in-frame, it is possible to distinguish the cells that will reach a particular differentiation stage to express the differentiation marker, by the expression of the labeling gene. A modification of the target gene on the chromosome can be performed using methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

Specifically, for example, a genomic gene for a target gene to be modified (for example, histocompatibility antigen genes, disease-related genes and the like) is isolated, and a target vector for homologous recombination of the target gene is prepared using the genomic gene isolated. The target vector prepared is introduced into an embryonic stem cell, and cells undergoing homologous recombination between the target gene and the target vector are selected, whereby embryonic stem cells having a modified gene on the chromosome thereof can be prepared.

As methods of isolating a genomic gene of a target gene, publicly known methods described in Molecular Cloning, A Laboratory Manual, Second Edition, Cold Spring Harbor Laboratory Press (1989), Current Protocols in Molecular Biology, John Wiley & Sons (1987-1997) and elsewhere can be mentioned. By using a genomic DNA library screening system (produced by Genome Systems), Universal GenomeWalker Kits (produced by CLONTECH) and the like, a genomic gene of a target gene can also be isolated.

Preparation of a Target Vector for Homologous recombination of a target gene and efficient selection of a homologous recombinant can be achieved according to methods described in Gene Targeting, A Practical Approach, IRL Press at Oxford University Press (1993); Biomanual Series 8 Gene Targeting, Preparation of Mutant Mice Using ES Cells, Yodosha (1995) and elsewhere. The target vector used may be any one of the replacement type and the insertion type; regarding methods of selection, positive selection, promoter selection, negative selection, poly A selection and the like can be used.

As methods of selecting a desired homologous recombinant from among sorted cell lines, Southern hybridization, PCR and the like for genomic DNA can be mentioned.

Also, embryonic stem cells are available from specified organizations, and commercial products may be purchased. For example, the human embryonic stem cells KhES-1, KhES-2 and KhES-3 are available from the Institute for Frontier Medical Sciences, Kyoto University.

Herein, induced pluripotent stem cells obtained by introducing into a somatic cell such as a skin cell a plurality of particular genes that are important to the maintenance of the multipotency and high proliferation capacity of ES cells can also be included in embryonic stem cells useful in a method of the present invention (Cell, 126, 1-14, 2006; Cell, 131, 1-12, 2007; Science, 318, no. 5858, 1917-1920; Nat. Biotechnol. 2008 January; 26(1):101-106. Epub 2007 Nov. 30; Nature, 451,141-146, 2008. Epub 2007 Dec. 23; others). Furthermore, fused ES cells obtained by cell fusion of an ES cell and a somatic cell can also be included in embryonic stem cells useful in a method of the present invention.

Embryonic stem cells can be maintained in culture by a method known per se. For example, embryonic stem cells can be maintained by culture without feeder cells with the addition of fetal calf serum (FCS), Knockout™ Serum Replacement (KSR), and LIF.

(2. Production of Retinal Progenitor Cells)

The present invention provides a method of producing retinal progenitor cells from embryonic stem cells. A method of the present invention for producing retinal progenitor cells comprises culturing embryonic stem cells as suspended aggregates in a medium containing or not containing serum, and obtaining retinal progenitor cells from the culture. Production of retinal progenitor cells from embryonic stem cells can be achieved in accordance with, for example, a method described in Nat. Neurosci. 8, 288-296 (2005). However, according to the animal species from which the embryonic stem cells are derived and the kind of desired retinal progenitor cells, culture conditions can be altered as appropriate. Hereinafter, the method is described in detail.

A retinal progenitor cell refers to a progenitor cell committed to differentiate into cells present in the retina [neural retina (inner membrane), retinal pigment epithelium (RPE, outer layer)]. As retinal progenitor cells, neural retinal progenitor cells and retinal pigment epithelium progenitor cells can be mentioned.

Whether or not the cells obtained are retinal progenitor cells can be determined by a method known per se, for example, the expression of a retinal progenitor cell marker. As examples of the retinal progenitor cell marker, Pax6 (neural retinal progenitor cells, retinal pigment epithelium progenitor cells), Rx (neural retinal progenitor cells), and Mitf (retinal pigment epithelium progenitor cells) can be mentioned.

"Culturing embryonic stem cells as suspended aggregates" refers to culturing a group of embryonic stem cells that have gathered and formed a mass in a culture medium under conditions that are non-adhesive to the cell culture vessel. Hereinafter, a culture like this is abbreviated as suspension culture as required.

When embryonic stem cells are suspension-cultured, to facilitate the formation of suspended aggregates, and/or to achieve efficient induction of differentiation, the culture is preferably performed in the absence of feeder cells.

A medium used in the suspension culture can be prepared with a medium for animal cell culture as the basal medium. The basal medium is not particularly limited, as far as it is a medium that can be used for animal cell culture; for example, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, Ham medium, RPMI 1640 medium, Fischer's medium, and a mixed medium thereof and the like can be mentioned.

When embryonic stem cells are suspension-cultured, a serum-free medium or a serum-containing medium is used as the medium. Here, a serum-free medium means a medium not containing unprepared or non-purified serum; a medium containing a purified blood-derived component or animal tissue-derived component (for example, growth factor) is to be construed as being a serum-free medium. As the serum, a serum derived from an optionally chosen animal, preferably a mammal, can be used. The mammal from which the serum is derived is the same as the mammal from which the embryonic stem cells are derived (described above).

When a serum-containing medium is used in the suspension culture, the concentration of the serum is not limited, as far as it is a concentration such that retinal progenitor cells can be efficiently differentiated; the concentration can be, for example, 0.5 to 30% (v/v), preferably about 1.0 to 20% (v/v), more preferably about 3 to 10% (v/v), and most preferably about 5% (v/v).

When retinal progenitor cells are produced from embryonic stem cells of a rodent such as a mouse, serum is an essential factor. If serum is not added, efficient differentiation of retinal progenitor cells from embryonic stem cells cannot be induced. The timing for addition of serum to the medium containing suspended aggregates of embryonic stem cells is not particularly limited, as far as it allows differentiation into retinal progenitor cells; the timing is, for example, within 3 to 7 days from the start of suspension culture. The serum may be added to the medium already at the start of suspension culture.

Meanwhile, when retinal progenitor cells are produced from embryonic stem cells of a primate such as a human or a monkey, serum is not an essential factor; primate retinal progenitor cells can be efficiently induced by performing the suspension culture in a serum-free medium over the entire period thereof. When the retinal progenitor cells produced are used for transplantation therapy and the like, a serum-free medium is preferably used, taking into account the risk of serum contamination with virus and the like.

The serum-free medium used in the suspension culture can be, for example, one containing a serum replacement. The serum replacement can, for example, be one containing as appropriate an albumin (for example, lipid-rich albumin), transferrin, fatty acids, insulin, collagen precursor, trace elements, 2-mercaptoethanol or 3'-thiolglycerol, or their equivalents and the like. Such a serum replacement can be prepared by, for example, a method described in WO98/30679. To facilitate easier implementation of a method of the present invention, commercially available serum substitutes can be utilized. As examples of such commercially available serum substitutes, knockout Serum Replacement (KSR), Chemically-defined Lipid concentrated (produced by Gibco) and Glutamax (produced by Gibco) can be mentioned.

The medium used in suspension culture can contain fatty acids or lipids, amino acids (for example, non-essential amino acids), vitamins, growth factors, cytokines, anti-oxidants, 2-mercaptoethanol, pyruvic acid, buffering agents, inorganic salts, additives (N2 supplement and the like) and the like. For example, 2-mercaptoethanol can be used without limitations, as far as it is used at a concentration suitable for culturing embryonic stem cells, and it can be used at concentrations of, for example, about 0.05 to 1.0 mM, preferably about 0.1 to 0.5 mM, more preferably about 0.2 mM.

The medium used for the suspension culture is not particularly limited, as far as it is as described above. However, from the viewpoint of avoiding painstakingness in preparation, as the medium, a serum-free medium (GMEM or dMEM, 0.1 mM 2-mercaptoethanol, 0.1 mM non-essential amino acids Mix, 1 mM sodium pyruvate) supplemented with an appropriate amount (for example, 1-20%) of commercially available KSR, and a serum-containing medium prepared by adding to this serum-free medium an appropriate amount (for example, 1-20%) of fetal bovine serum can be used.

To improve and stabilize the efficiency of differentiation into retinal progenitor cells, the medium used for the suspension culture preferably comprises any one inhibitor selected from the group consisting of a Nodal signal inhibitor and a Wnt signal inhibitor. Combination use of an Nodal signal inhibitor and a Wnt signal inhibitor is expected to have a still more remarkable effect.

The Nodal signal inhibitor is not particularly limited, as far as it is capable of suppressing Nodal-mediated signal transduction. As examples of the Nodal signal inhibitor, Lefty-A, Lefty-B, Lefty-1, Lefty-2, soluble Nodal receptor, Nodal antibody, Nodal receptor inhibitor, and SB-431242 can be mentioned.

SB-431242 is a publicly known compound that inhibits ALK4, ALK5 and ALK7 selectively, having the structure shown below.

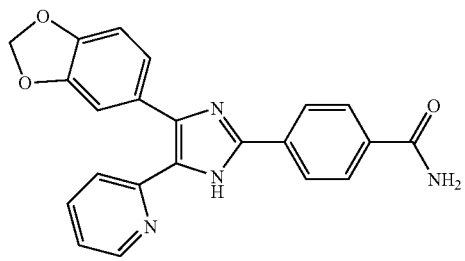 [SMILES: NC(=O)c1ccc(-c2nc(-c3ccc4c(c3)OCO4)c(-c3ccccn3)[nH]2)cc1]

The concentration of the Nodal signal inhibitor used in the suspension culture can be a concentration such that promotion of the differentiation of suspended aggregates into retinal progenitor cells or the above-described utility can be accomplished. The concentration can be, for example, about 0.1 to 100 µg/ml, preferably about 0.5 to 50 µg/ml, for Lefty-A. For SB-431242, the concentration can be about 0.01 to 100 µM, preferably 0.1 to 10 µM.

The Wnt signal inhibitor is not particularly limited, as far as it is capable of suppressing Wnt-mediated signal transduction. As examples of the Wnt signal inhibitor, Dkk1, Cerberus protein, Wnt receptor inhibitor, soluble Wnt receptor, Wnt antibody, casein kinase inhibitor, dominant negative Wnt protein, CKI-7 (N-(2-aminoethyl)-5-chloro-isoquinoline-8-sulfonamide), and D4476 (4-{4-(2,3-dihydrobenzo[1,4]dioxyn-6-yl)-5-pyridin-2-yl-1H-imidazol-2-yl}benzamide) can be mentioned.

CKI-7 and D4476 are commonly known compounds that inhibit casein kinase 1 selectively.

The concentration of the Wnt signal inhibitor used in the suspension culture can be a concentration such that promotion of the differentiation of suspended aggregates into retinal progenitor cells or the above-described utility can be accomplished. The concentration can be, for example, about 0.05 to 20 µg/ml, preferably about 0.1 to 10 µg/ml, for Dkk1. For CKI-7, the concentration can be about 0.1 to 100 µM, preferably 1 to 10 µM. For D4476, the concentration can be about 0.1 to 100 µM, preferably 1 to 10 µM.

In the present invention, when a Nodal signal inhibitor and a Wnt signal inhibitor are used in combination, preferred combinations thereof include, but are not limited to, Lefty-A and Dkk1; SB-431242 and CKI-7; SB-431242 and D4476, and the like.

Although the Nodal signal inhibitor and/or the Wnt signal inhibitor may be added to the medium already at the start of cultivation of embryonic stem cells, it can be added to the medium several days after the start of cultivation (for example, at a time within 10 days of cultivation). Preferably, the Nodal signal inhibitor and/or the Wnt signal inhibitor is added to the medium at a time within 5 days of cultivation.

In particular, when the suspended culture is performed in a serum-free medium, the medium preferably contains at least one (preferably both) inhibitor selected from the group consisting of a Nodal signal inhibitor and a Wnt signal inhibitor. With the addition of these inhibitors, it is possible to efficiently produce retinal progenitor cells from primate embryonic stem cells even when a serum-free medium is used over the entire period of the suspension culture.

Suspension culture of embryonic stem cells can of course be performed in the absence of a Nodal signal inhibitor and/or a Wnt signal inhibitor. It is also possible to switch the culture conditions during the suspension culture.

For the purpose of promoting differentiation into retinal progenitor cells, activin (for example, activin A) may be added to the medium used for the suspension culture. The concentration of activin used for the suspension culture can be a concentration such that retinal progenitor cells can be more efficiently produced. The concentration can be, for example, about 1 to 10000 ng/ml, preferably about 10 to 1000 ng/ml.

The timing for addition of activin to the medium containing suspended aggregates of embryonic stem cells is not particularly limited, as far as it allows differentiation into retinal progenitor cells; the timing is, for example, within 7 days from the start of the suspension culture (for example, 3 to 7 days later).

Suspension culture of embryonic stem cells can of course be performed in the absence of activin. It is also possible to switch this culture condition during the suspension culture.

In a preferred embodiment, to perform differentiation from embryonic stem cells to retinal progenitor cells particularly efficiently, suspension culture is performed in a medium containing serum, a Nodal signal inhibitor, a Wnt inhibitor and activin. This method is suitable particularly for producing retinal progenitor cells from embryonic stem cells of a rodent such as a mouse.

In another preferred embodiment, to achieve differentiation from embryonic stem cells to retinal progenitor cells particularly efficiently, suspension culture is performed in a serum-free medium containing a Nodal signal inhibitor and a Wnt inhibitor. This method is suitable particularly for producing retinal progenitor cells from embryonic stem cells of a primate such as a human or monkey; use of this method makes it possible to induce retinal progenitor cells in a serum-free medium, which has been difficult for mouse embryonic stem cells, for embryonic stem cells of a primate such as a human.

The culture vessel used for the suspension culture is not particularly limited, as far as it allows suspension culture of cells; examples include flasks, tissue culture flasks, dishes, Petri dishes, tissue culture dishes, multi-dishes, microplates, micro-well plates, multi-plates, multi-well plates, chamber slides, Petri dishes, tubes, trays, culturing bags, and roller bottles.

When embryonic stem cells are suspension-cultured, the culture vessel is preferably non-adhesive to cells. As the non-adhesive-to-cell culture vessel, a culture vessel whose surface has not been artificially treated for the purpose of increasing the adhesiveness to cells (for example, coating treatment with extracellular matrix and the like) can be used.

At the start of cultivation, maintenance-cultured embryonic stem cells are dispersed, and these are again seeded into a culture vessel. Depending on the animal species from which the embryonic stem cells are derived, the production efficiency for retinal progenitor cells is largely influenced by the degree of the dispersing treatment. In the case of a rodent such as a mouse, retinal progenitor cells can be induced with high efficiency even when the maintenance-cultured embryonic stem cells are vigorously dispersed to single cells, or even when they are weakly dispersed to obtain a large aggregate exceeding 50 cells per aggregate. Meanwhile, in the case of a primate, the stem cells are prepared so that each aggregate will be preferably configured with 2 to 50, more preferably 2 to 20, still more preferably 5 to 10 embryonic stem cells. If embryonic stem cells are dispersed to single cells, the cell viability declines, and the induction efficiency for retinal progenitor cells declines. If the number of embryonic stem cells per aggregate exceeds 50, the induction efficiency for retinal progenitor cells can decline.

At the start of cultivation, an embryonic stem cell concentration can be set as appropriate so that suspended aggregates of embryonic stem cells will be more efficiently formed. At the start of cultivation, the embryonic stem cell concentration is not particularly limited, as far as it is a concentration that allows the formation of suspended aggregates of embryonic stem cells, and the concentration can be, for example, about $1 \times 10^3$ to about $5 \times 10^6$ cells/ml, preferably about $3 \times 10^4$ to about $1 \times 10^5$ cells/ml (based on aggregate concentration, about $1 \times 10^3$ to about $1 \times 10^5$/ml, preferably about $3 \times 10^3$ to about $2 \times 10^4$/ml).

Other culture conditions such as culture temperature and $CO_2$ concentration in the suspension culture can be set as appropriate. Culture temperature is not particularly limited, and is, for example, about 30 to 40° C., preferably about 37° C. The $CO_2$ concentration is, for example, about 1 to 10%, preferably about 5%.

The period of the suspension culture can be of a length that allows retinal progenitor cells to be produced more efficiently. The length of the period can be, for example, about 3 days or more, preferably about 3 to 40 days, and more preferably about 5 to 25 days. In particular, in inducing retinal progenitor cells from embryonic stem cells of a primate efficiently, the duration of the suspension culture is preferably 15 days or more (for example, about 16 to 25 days).

After the suspension culture, the aggregates may be allowed to stand as they are, or subjected to a dispersing treatment (for example, trypsin/EDTA treatment), and the cells may be then further cultured under adhesive conditions (hereinafter, abbreviated as adhesion culture as required). In adhesion culture, it is preferable to use an adhesive-to-cell culture vessel, for example, a culture vessel coated with an extracellular matrix and the like (for example, poly-D lysine, laminin, fibronectin, collagen, poly-L lysine, polyethylenimine, polyornithine, Matrigel and the like). Also, culture conditions such as culture temperature and $CO_2$ concentration in the adhesion culture can be set as appropriate as with the conditions for suspension culture. A medium for the adhesion culture can be chosen as appropriate as with the medium for the suspension culture, except that the medium need not contain a Nodal signal inhibitor, a Wnt signal inhibitor and activin.

The period of the adhesion culture can be of a length that allows retinal progenitor cells to be produced more efficiently. The length of the period can be, for example, about 3 days or more, preferably about 3 to 70 days, and more preferably about 5 to 40 days.

After completion of the cultivation, retinal progenitor cells can be isolated from the culture. This isolation can be performed using an antibody against the above-described retinal progenitor cell marker and the like, by a method known per se (cell sorter and the like). Alternatively, the isolation can be performed using a cell having a labeling gene (for example, fluorescent protein such as GFP) knocked in a gene that encodes a retinal progenitor cell marker (for example, Rx) in-frame, as the embryonic stem cell, with the expression of the labeling gene as an index, by a method known per se (cell sorter and the like).

The culture obtained by a method of the present invention contains retinal progenitor cells at high frequency (content amount). Cells obtained by a method of the present invention are Rx-positive (neural retinal progenitor cell marker) at high frequency, for example, at a frequency (colony frequency) of 5% or more, preferably 10 to 50%. These Rx-positive cells are mostly (for example, 90% or more) Pax6-positive in consistence with the profile of neural retinal progenitor cells.

Also, cells obtained by a method of the present invention are Mitf-positive (retinal pigment epithelium progenitor cell marker) at high frequency, for example, at a frequency (colony frequency) of 5% or more, preferably 10 to 60%. These Mitf-positive cells are mostly (for example, 90% or more) Pax6-positive in agreement with the profile of retinal pigment epithelium of the embryo.

According to a method of the present invention, by performing the cultivation in a serum-free medium over the entire period thereof, it is possible to produce primate retinal progenitor cells with high efficiency.

(3. Production of Retinal Pigment Epithelial Cells)

The present invention provides a method of producing retinal pigment epithelial cells. In the same manner as the above-described method of producing retinal progenitor cells, by culturing embryonic stem cells as suspended aggregates in a medium containing or not containing serum, further culturing the cultured cells under adhesive conditions, and obtaining retinal pigment epithelial cells from the culture, retinal pigment epithelial cells can be produced.

Retinal pigment epithelial cells are epithelial cells that constitute the retinal pigment epithelium. It can be determined whether or not the cells obtained are retinal pigment epithelial cells, by a method known per se, for example, the expression of a retinal pigment epithelial cell marker. As examples of the retinal pigment epithelial cell marker, RPE-65 can be mentioned. Besides, with cell morphology (intracellular melanin pigment deposition, polygonal and flat cell morphology, polygonal actin bundle formation and the like) as an index, using a light microscope, it is possible to determine whether or not the cells obtained are retinal pigment epithelial cells.

In the production of retinal pigment epithelial cells, the conditions for suspension culture and adhesion culture are the same as those for production of retinal progenitor cells, except for the length of the period of adhesion culture. The period of adhesion culture in the production of retinal pigment epithelial cells can be of a length such that retinal pigment epithelial cells can be more efficiently produced. The length of the period can be, for example, about 10 days or more, preferably about 20 to 120 days, more preferably about 30 to 100 days. By this long-term adhesion culture, differentiation from retinal progenitor cells (retinal pigment epithelium progenitor cells) produced by the method 2 above into retinal pigment epithelial cells is further induced.

After completion of the adhesion culture, retinal pigment epithelial cells can be isolated from the culture. This isolation can be performed using an antibody against the above-described retinal pigment epithelial cell marker and the like, by a method known per se (cell sorter and the like).

The culture obtained by a method of the present invention contains retinal pigment epithelial cells at high frequency (content amount). Cells obtained by a method of the present invention cells are frequently, for example, at a frequency (colony frequency) of 5% or more, preferably 10 to 60%, positive for RPE-65 (retinal pigment epithelial cell marker). These cells have typical characteristics of mature retinal pigment epithelium, such as a flat polygonal morphology, bipolarization accompanied by terminal microvilli and basement membrane, the presence of melanin granules, and the presence of tight junctions and adhesive linkage.

According to a method of the present invention, by performing the cultivation in a serum-free medium over the entire period thereof, primate retinal pigment epithelial cells can be produced with high efficiency.

(4. Production of Photoreceptors or a Precursor Thereof)

The present invention provides a method of producing photoreceptors or a precursor thereof. In the same manner as the above-described method of producing retinal progenitor cells, by culturing embryonic stem cells as suspended aggregates in a medium containing or not containing serum, further culturing the cultured cells under adhesive conditions, and obtaining photoreceptors or a precursor thereof from the culture, photoreceptors or a precursor thereof can be produced.

A photoreceptor precursor is a progenitor cell committed to differentiate into photoreceptor. It can be determined whether or not the cells obtained are photoreceptor precursor, by a method known per se, for example, the expression of a photoreceptor precursor marker. As examples of the photoreceptor precursor marker, Crx can be mentioned.

Visual cells include rod photoreceptor and cone photoreceptor. It can be determined whether or not the cells obtained are photoreceptors, by a method known per se, for example, the expression of a photoreceptor marker. As examples of the photoreceptor marker, rhodopsin (rod photoreceptors), red/green opsin (cone photoreceptors), blue opsin (cone photoreceptors), Recoverin (rod photoreceptors, cone photoreceptors) and the like can be mentioned.

In the production of photoreceptors or a precursor thereof, the conditions for suspension culture and adhesion culture are the same as those for production of retinal progenitor cells (2 above) except for the period of adhesion culture. In the production of photoreceptors or a precursor thereof, the period of adhesion culture can be of a length such that photoreceptors or a precursor thereof can be more efficiently produced. The length of the period is, for example, about 10 days or more, preferably 15 days to 300 days. In particular, the culturing period in the production of primate photoreceptors or progenitor cells thereof can be longer than that for rodents (about 30 days or more, preferably about 40 to 300 days, more preferably about 50 to 200 days). By this adhesion culture, differentiation from retinal progenitor cells (neural retinal progenitor cells) produced by the above-described method to a photoreceptor precursor and photoreceptors is further induced.

To promote differentiation into photoreceptors or a precursor thereof, in the production of photoreceptors or a precursor thereof, adhesion culture is preferably performed in a medium containing at least one (for example, two, preferably three, more preferably four, most preferably five) factor selected from the group consisting of an FGF (aFGF, bFGF and the like), an shh signal promoter, retinoic acid and taurine. In particular, in the production of primate photoreceptor or a precursor thereof, it is preferable that adhesion culture be performed in a medium comprising retinoic acid and/or taurine. By using a plurality of these factors in combination, an even more remarkable effect is expected.

The concentration of FGF used in the adhesion culture is not limited, as far as it is capable of promoting differentiation into photoreceptors or a precursor thereof, and the concentration is, for example, about 0.1 to 1000 ng/ml, preferably about 1 to 500 ng/ml, and more preferably about 5 to 200 ng/ml.

The Shh signal promoter is not particularly limited, as far as it is capable of enhancing Shh-mediated signal transduction. As examples of the Shh signal promoter, proteins belonging to the Hedgehog family (for example, Shh), Shh receptors, and Shh receptor agonists can be mentioned, and Shh in particular is preferable.

The concentration of the Shh signal promoter in the adhesion culture is not limited, as far as it is capable of promoting differentiation into photoreceptors or a precursor thereof. The concentration can be, for example, about 0.1 to 1000 nM, preferably about 0.3 to 100 nM, more preferably about 1 to 50 nM.

The concentration of the retinoic acid used in the adhesion culture is not limited, as far as it is capable of promoting differentiation into photoreceptors or a precursor thereof. The concentration can be, for example, about 1 to 10000 nM, preferably about 10 to 2000 nM, more preferably about 100 to 1000 nM.

The concentration of the taurine used in the adhesion culture is not limited, as far as it is capable of promoting differentiation into photoreceptors or a precursor thereof. The concentration can be, for example, about 5 to 2000 μM, more preferably about 10 to 1000 μM.

Although the above-described factors may be added to the medium already at the start of the adhesion culture, it is preferable that the factors be added to the culture at a stage after the emergence of a photoreceptor precursor in the culture (for example, from 3 days, preferably from 7 days after the start of the adhesion culture). Thereby, differentiation from a photoreceptor precursor to photoreceptors is efficiently promoted.

To promote differentiation into photoreceptors or a precursor thereof, the adhesion culture in the production of photoreceptors or a precursor thereof is preferably performed in a medium containing additives (N2 supplement and the like). An additive concentration in the medium can be set as appropriate within a range of concentrations in common use by those skilled in the art.

The adhesion culture can of course be performed in the absence of the above-described factor. It is also possible to switch these culture conditions during the adhesion culture.

After completion of the adhesion culture, photoreceptors or a precursor thereof can be isolated from the culture. This isolation can be performed using an antibody against the above-described marker for photoreceptors or a precursor thereof and the like by a method known per se (cell sorter and the like). Alternatively, the isolation can be performed using a cell having a labeling gene (for example, fluorescent protein such as GFP) knocked in a gene that encodes a marker of photoreceptors or a precursor thereof (for example, Rx) in-frame, as the embryonic stem cell, with the expression of the labeling gene as an index, by a method known per se (cell sorter and the like).

The culture obtained by a method of the present invention contains photoreceptors or a precursor thereof at high frequency (content amount). Cells obtained by a method of the present invention are Crx-positive (photoreceptor precursor marker) at high frequency, for example, at a frequency (colony frequency) of 5% or more, preferably 10 to 40%. Photoreceptors obtained a method of the present invention are rhodopsin-positive (photoreceptor marker) at high frequency, for example, at a frequency (colony frequency) of 5% or more, preferably 10 to 40%. These rhodopsin-positive cells can be Recoverin-positive.

According to a method of the present invention, by performing the cultivation in a serum-free medium over the entire period thereof, primate photoreceptors or a precursor thereof can be produced with high efficiency.

(5. Production of Photoreceptor Precursor or Cone Photoreceptors)

The present invention provides a method of producing photoreceptor precursors or cone photoreceptors, comprising culturing isolated retinal progenitor cells differentiated from an embryonic stem cell under adhesive conditions in the presence of a gamma secretase inhibitor, and obtaining a photoreceptor precursor or cone photoreceptors from the culture. A gamma secretase inhibitor induces differentiation from retinal progenitor cells into photoreceptor precursors, and at the same time potently promotes differentiation from photoreceptor precursors to cone photoreceptors. Importantly, gamma secretase inhibitors do not induce differentiation from photoreceptor precursor cells to rod photoreceptors. Therefore, using this method, it is possible to selectively produce cone photoreceptors while suppressing the contamination with rod photoreceptors to the minimum extent.

As retinal progenitor cells differentiated from an embryonic stem cells, for example, retinal progenitor cells (particularly, neural retinal progenitor cells) differentiated from an embryonic stem cell in vitro by the method 1 described above or a method described in Nat. Neurosci. 8, 288-296 (2005) can be used.

The retinal progenitor cells used in this method need to be isolated. If non-isolated retinal progenitor cells are used, the effect of the gamma secretase inhibitor in promoting differentiation into a photoreceptor precursor and cone photoreceptors, is weakened.

Herein, "isolated" means that an operation has been conducted to increase the purity (ratio) of desired cells compared with that obtained without the operation. The purity of isolated cells (ratio of desired cells in all cells) is, for example, 60% or more, preferably 70% or more, more preferably 80% or more, and most preferably 90% or more (for example, 100%).

Isolation of retinal progenitor cells can be performed using an antibody against the above-described retinal progenitor cell marker and the like, by a method known per se (cell sorter and the like). Alternatively, the isolation can be performed using as the embryonic stem cell a cell having a labeling gene (for example, fluorescent proteins such as GFP) knocked in a gene that encodes a retinal progenitor cell marker (for example, Rx) in-frame, with the expression of the labeling gene as an index, by a method known per se (cell sorter and the like).

Next, isolated retinal progenitor cells are cultured under adhesive conditions in the presence of a gamma secretase inhibitor. In this adhesion culture, it is preferable that the isolated retinal progenitor cells be re-aggregated by centrifugation and the like, and that aggregates of retinal progenitor cells be seeded. The conditions for the adhesion culture are the same as those for 1 above, except that a gamma secretase inhibitor is added to the medium.

As examples of the gamma secretase inhibitor, N—[N-(3, 5-difluorophenacetyl)-L-alanyl]-S-phenylglycine t-butyl ester (DAPT) can be mentioned.

The concentration of the gamma secretase inhibitor used in the adhesion culture can be a concentration that can promote differentiation from retinal progenitor cells to photoreceptor precursors or cone photoreceptors. This concentration can be, for example, about 0.1 to 1000 µM, preferably about 1 to 100 µM, more preferably about 30 to 50 µM.

Although the gamma secretase inhibitor may be added to the medium already at the start of the adhesion culture, it is preferably added to the culture several days after the start of the adhesion culture (for example, at a time within 10 days of the culture). Preferably, the gamma secretase inhibitor is added at a time within 5 days of the culture, more preferably within 2 days.

The period of adhesion culture in the presence of a gamma secretase inhibitor can be of a length such that photoreceptor precursors or cone photoreceptors can be more efficiently produced. The length of the period can be, for example, about 3 days or more, preferably about 5 to 100 days, more preferably about 10 to 50 days.

It can be determined whether or not the cells obtained are photoreceptor precursors, by a method known per se, for example, the expression of a photoreceptor precursor marker. As examples of the photoreceptor precursor marker, Crx can be mentioned.

It can be determined whether or not the cells obtained are cone photoreceptors, by a method known per se, for example, the expression of a cone photoreceptor marker. As examples of the photoreceptor marker, red/green opsin (cone photoreceptors), blue opsin (cone photoreceptors), Recoverin (rod photoreceptors, cone photoreceptors) and the like can be mentioned.

After completion of the adhesion culture, a photoreceptor precursor or cone photoreceptor can be isolated from the culture. This isolation can be achieved using an antibody against the above-described photoreceptor precursor or cone photoreceptor marker and the like, by a method known per se (cell sorter and the like).

The culture obtained by a method of the present invention contains photoreceptor precursors or cone photoreceptors at high frequency (content amount). Cells obtained by a method of the present invention are Crx-positive (photoreceptor precursor marker) at high frequency, for example, at a frequency (colony frequency) of 5% or more, preferably 10 to 30%. Cells obtained by a method of the present invention are also opsin (red/green opsin, or blue opsin)-positive (photoreceptor marker) at high frequency, for example, at a frequency (colony frequency) of 5% or more, preferably 10 to 30%.

(6. Production of Rod Photoreceptors)

The present invention provides a method of producing rod photoreceptors, comprising culturing isolated retinal progenitor cells differentiated from embryonic stem cells, under adhesive conditions in the presence of a gamma secretase inhibitor, further culturing the cultured cells under adhesive conditions in the presence of at least any one factor selected from the group consisting of an FGF, an shh signal promoter, retinoic acid and taurine, and obtaining rod photoreceptors from the culture. As stated in 5 above, differentiation into rod photoreceptors is not promoted by the addition of a gamma secretase inhibitor. However, by treating the cultured cells with the aforementioned factor after the cultivation in the presence of a gamma secretase inhibitor, differentiation into rod photoreceptors can be promoted.

The steps until the cultivation under adhesive conditions in the presence of a gamma secretase inhibitor can be performed in the same manner as 5 above. The cells obtained by this step are further cultured under adhesive conditions in a medium containing at least one (for example, two, preferably three, more preferably four, most preferably five) factor selected from the group consisting of an FGF (aFGF, bFGF and the like), an shh signal promoter, retinoic acid and taurine. By using a plurality of these factors in combination, an even more remarkable effect is expected.

The choices and concentrations of the FGF, shh signal promoter, retinoic acid and taurine and adhesion conditions used for the cultivation are the same as those for 4 above.

The period of adhesion culture after addition of these factors can be of a length such that rod photoreceptors can be more efficiently produced. The length of the period can be, for example, about 5 days or more, preferably about 8 to 50 days.

In this further cultivation, in addition to the above-described factor, a gamma secretase inhibitor such as DAPT may be added to the medium. By the addition of a gamma secretase inhibitor, the differentiation of rod photoreceptors can be promoted.

In this case, the concentration of the gamma secretase inhibitor can be a concentration such that differentiation of rod photoreceptors can be promoted. This concentration can be, for example, about 0.1 to 1000 µM, preferably about 1 to 100 µM, more preferably about 30 to 50 µM.

To promote differentiation into rod photoreceptors, this further cultivation is preferably performed in a medium containing additives (N2 supplement and the like). The additive concentrations in the medium can be set as appropriate within a range of concentrations in common use by those skilled in the art.

It can be determined whether the cells obtained are rod photoreceptors, by a method known per se, for example, the expression of a rod photoreceptor marker. As examples of the rod photoreceptor marker, rhodopsin, Recoverin and the like can be mentioned.

After completion of the adhesion culture, rod photoreceptors can be isolated from the culture. This isolation can be achieved using an antibody against the above-described photoreceptor precursor or rod photoreceptor marker and the like by a method known per se (cell sorter and the like).

In the culture obtained by a method of the present invention, rod photoreceptors are contained at high frequency (content). Cells obtained by a method of the present invention are rhodopsin-positive at high frequency, for example, at a high frequency (colony frequency) of 5% or more, preferably 10 to 30%. These rhodopsin-positive cells are co-expressing Recoverin.

(7. Cell Culture and Use as Pharmaceutical)

The present invention also provides a cell culture obtained by a method of the present invention. The cell culture of the present invention can be, for example, suspended aggregates of embryonic stem cells, cells prepared by dispersing suspended aggregates, cells obtained from a culture of dispersed cells and the like. The present invention also provides homogenous cells, for example, retinal progenitor cells (neural retinal progenitor cells, retinal pigment epithelium progenitor cells), photoreceptor precursor, and photoreceptors (cone photoreceptors, rod photoreceptors), that have been isolated/purified from such a culture to the extent that allows administration to a subject.

Cells obtained by a method of the present invention can be used as therapeutic drugs for retinal diseases such as age-related macular degeneration, retinitis pigmentosa, diabetic retinopathy, and retinal detachment, or for replenishing retinal cells in a state where the cells are damaged due to other causes, and for other purposes.

When cells obtained by a method of the present invention are used as a therapeutic drug for retinal disease, it is preferable that the cells be transplanted to the subject after being made to have increased purity.

Any method of cell separation and purification in public knowledge can be used; for example, a method using a flow cytometer (see, for example, Antibodies—A Laboratory Manual, Cold Spring Harbor Laboratory (1988), Monoclonal Antibodies: principles and practice, Third Edition, Acad. Press (1993), Int. Immunol., 10, 275 (1998)), the panning method (see, for example, Monoclonal Antibodies: principles and practice, Third Edition, Acad. Press (1993), Antibody Engineering, A Practical Approach, IRL Press at Oxford University Press (1996), J. Immunol., 141, 2797 (1988)), and cell fractionation based on sucrose density differences (see, for example, Soshiki Baiyou no Gijyutsu (3rd edition), Asakura Shoten (1996)) can be mentioned.

In transplantation therapy, graft rejection due to histocompatibility antigen differences is often problematic, which problem, however, can be solved by using an embryonic stem cell having the nucleus of a somatic cell transplanted thereto, or an embryonic stem cell having a modified gene on the chromosome thereof.

By inducing differentiation using an embryonic stem cell having the nucleus of a somatic cell transplanted thereto, cells of the individual being the donor of the somatic cell, for example, photoreceptors, can be obtained. Cells of an individual like this are not only effective in transplantation medicine as they are, but also useful as a diagnostic material in determining whether an existing drug is effective on the individual.

Cells, for example, photoreceptors, differentiated from an embryonic stem cell can be transplanted to a diseased part of a patient's body by a method known per se (see, for example, Arch Opthalmol. 122, 1159-1165 (2004)).

The present invention is hereinafter described more specifically by means of the following Examples, to which, however, the invention is never limited.

EXAMPLES

Example 1

Methods

Cell Culture

Methods for mouse ES cell maintenance and differentiation in SFEB conditions were previously reported (reference documents A7, 20). For the sake of the SFEB/DLFA, Dkk1 (R & D Systems, 100 ng/ml, during days 0-5), LeftyA (R & D Systems, 500 ng/ml, during days 0-5), 5% FCS (JRH Biosciences, during days 3-5), and Activin-A (R & D Systems, 10 ng/ml, during days 4-5) were added to a differentiation medium (G-MEM, 5% KSR, 0.1 mM non-essential amino acids, 1 mM pyruvic acid, and 0.1 mM 2-mercaptoethanol) (reference document A6).

For FACS (see below), until day 9, cell aggregates were incubated in a differentiation medium under suspension culture conditions. After FACS, $1-2\times10^4$ sorted cells were re-suspended in a differentiation medium containing 10% FCS, and to produce re-aggregated pellets, the suspension was centrifuged at 800 g for 10 minutes. After cultivation at 37° C. for 1 hour, three to five re-aggregated pellets per $cm^2$ were replated on a poly-D-lysine/laminin/fibronectin-coated culture slides with a differentiation medium supplemented with 10% FCS. On day 10, the culture medium was changed to a differentiation medium not containing FCS, and containing or not containing the gamma secretase inhibitor N—[N-(3,5-difluorophenacetyl)-L-alanyl]-S-phenylglycine t-butyl ester (DAPT, 10 µM, Calbiochem).

Figure 3:
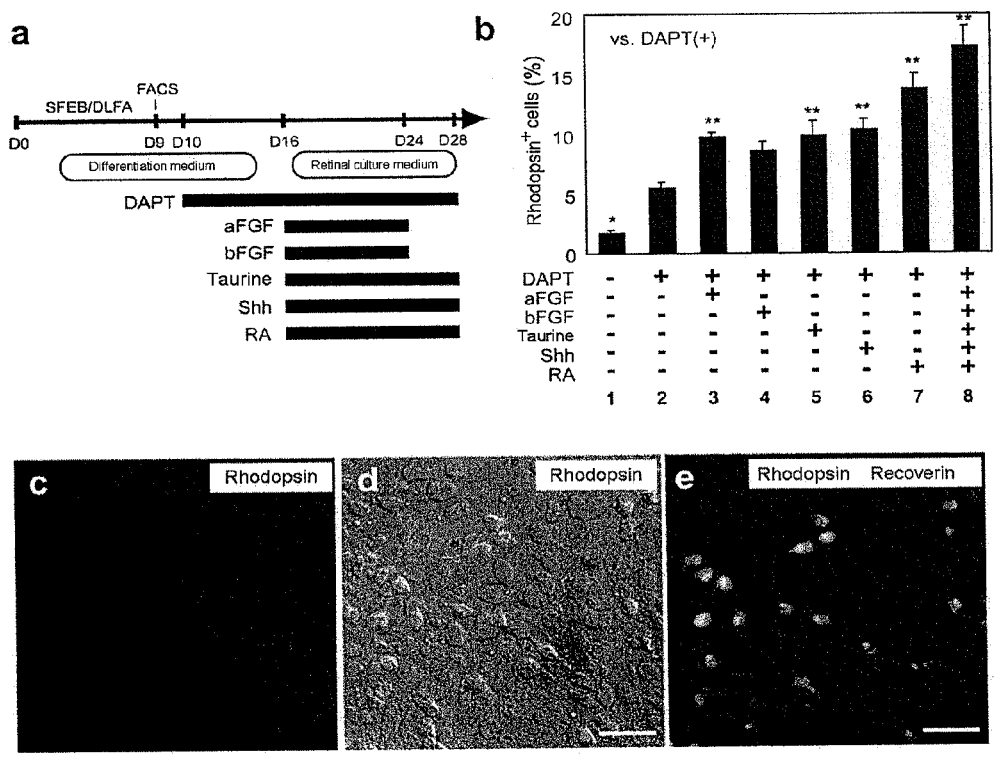
FIG. 3 Promotion of differentiation of $rhodopsin^+$ photoreceptors by FGF, taurine, shh and RA. (a) The procedure for differentiation of $rhodopsin^+$ cells from ES cells. (b) Sorted $Rx\text{-}GFP^+$ cells were treated with the indicated factors on day 16; on day 28, the percentage of $rhodopsin^+$ cells was determined. *, $P<0.05$, **, $P<0.01$, vs. DAPT (+) (lane 2), Dunnett's test. (c-e) Immunostaining of sorted cells treated with DAPT, aFGF, bFGF, taurine, shh and RA, on day 28. (c) Many cells expressed rhodopsin (red). (d, e) Merged view of rhodopsin staining (red) with Normarski image (d) or with Recoverin staining (green). Scale bar, 20 μm.

For photoreceptor differentiation, on day 16, the medium was replaced with a retinal culture medium containing the factors shown in FIG. 3a (66% E-MEM-HEPES (Sigma M7278), 33% HBSS (Gibco 24020-117), 1% FCS supplemented with N2, 5.75 mg/ml glucose, 200 µM L-glutamine, 100 U/ml penicillin, and 100 µg/ml streptomycin (Gibco)). aFGF (R & D Systems) and bFGF (R & D Systems) were added during differentiation for 16-24 days; taurine (Sigma), shh (R & D Systems), and RA (Sigma) were added during differentiation days 16-28. The medium was replaced with a fresh supply every 2 days.

BrdU uptake was examined by culturing the cells in a medium containing 5 µg/ml BrdU for 24 hours before fixation.

FACS Experiments

On day 9, SFEB/DLFA-treated ES cell aggregates were dissociated with trypsin (0.25%, Invitrogen) and DNaseI (10 µg/ml, Sigma) into single cells. After neutralization, the cells were re-suspended in HBSS containing 0.1% BSA and 5 µg/ml propidium iodide (PI, Sigma), and passed through a cell strainer (BD) as described previously (reference documents A7, 21). The cells were counted and sorted using FACS Aria (BD Biosciences), and data were analyzed using the FACS Diva software (BD Biosciences). Dead cells were excluded by gating forward and side scatter and PI staining. Cells with Rx-GFP fluorescence (band-pass filter: FITC, 530 nm) were sorted and further cultured.

RT-PCR

RT-PCR analysis was performed as reported previously (reference documents A7, 20). The primers used are as follows:

```
Notch1 (reference document A22)
Forward:
5'-TGCCTGTGCACACCATTCTGC-3'        (SEQ ID NO: 1)
Reverse:
5'-CAATCAGAGATGTTGGAATGC-3'        (SEQ ID NO: 2)

Notch2 (reference document A22)
Forward:
5'-ATGCACCATGACATCGTTCG-3'         (SEQ ID NO: 3)
Reverse:
5'-GATAGAGTCACTGAGCTCTCG-3'        (SEQ ID NO: 4)

Notch3 (reference document A22)
Forward:
5'-TTGGTCTGCTCAATCCTGTAGC-3'       (SEQ ID NO: 5)
Reverse:
5'-TGGCATTGGTAGCAGTTGCTG-3'        (SEQ ID NO: 6)

Notch4 (reference document A22)
Forward:
5'-AAGCGACACGTACGAGTCTGG-3'        (SEQ ID NO: 7)
Reverse:
5'-ATAGTTGCCAGCTACTTGTGG-3'        (SEQ ID NO: 8)

Hes1 (reference document A22)
Forward:
5'-TCTACACCAGCAACAGTGG-3'          (SEQ ID NO: 9)
Reverse:
5'-TCAAACATCTTTGGCATCAC-3'         (SEQ ID NO: 10)

Hes5 (reference document A22)
Forward:
5'-AAGTGACTTCTGCGAAGTTCC-3'        (SEQ ID NO: 11)
Reverse:
5'-AAGGCCATGTGGACCTTGAGG-3'        (SEQ ID NO: 12)

Hey1 (reference document A23)
Forward:
5'-TCGAGAAGCGCCGACGAGACCGA-3'      (SEQ ID NO: 13)
Reverse:
5'-CAGCAGAGGGTGTGCGATGTGTGGGT-3'   (SEQ ID NO: 14)

gnat1
Forward:
5'-GAGCTTAACATGCGACCTGA-3'         (SEQ ID NO: 15)
Reverse:
5'-GCTGCTGTAGGTCCAAGAGG-3'         (SEQ ID NO: 16)

pde6b
Forward:
5'-CATGAATGGCAAAGATGTCG-3'         (SEQ ID NO: 17)
Reverse:
5'-GTGTTCGTGGGCCTGAGTAT-3'         (SEQ ID NO: 18)

pde6c
Forward:
5'-GAGGTCCTTGCTGTGGTCAT-3'         (SEQ ID NO: 19)
Reverse:
5'-CCTTGTGAAACTGTCGCTCA-3'         (SEQ ID NO: 20)

cnga1
Forward:
5'-GAGCAAGGCCGATGATAAAA-3'         (SEQ ID NO: 21)
Reverse:
5'-TCACTAGCAGCCCTTGTTCC-3'         (SEQ ID NO: 22)

sag
Forward:
5'-GTCCTCACCCAACTCCAAGA-3'         (SEQ ID NO: 23)
Reverse:
5'-GTTGTTGGTCACGGTCACAG-3'         (SEQ ID NO: 24)

arr3
Forward:
5'-GTCCTTGTTGACCCCGAGTA-3'         (SEQ ID NO: 25)
Reverse:
5'-CTGCACTTTCCCTACAACCA-3'         (SEQ ID NO: 26)

Grk1
Forward:
5'-CTGCATCAGAGACGCATTGT-3'         (SEQ ID NO: 27)
Reverse:
5'-TCTCCAACAGCTGCTCACAG-3'         (SEQ ID NO: 28)

pdc
Forward:
5'-CACACAGGACCCAAAGGAGT-3'         (SEQ ID NO: 29)
Reverse:
5'-TCTGCTCCTTCTCGATGGTT-3'         (SEQ ID NO: 30)

rdh12
Forward:
5'-GGCCAATCTGCTCTTCACTC-3'         (SEQ ID NO: 31)
Reverse:
5'-TGAAAAGGCTCTGGTCTTCG-3'         (SEQ ID NO: 32)

rbp3
Forward:
5'-TTCCCTCCCCAGAAGTCTTT-3'         (SEQ ID NO: 33)
Reverse:
5'-GGATGGCTACGCTCTTCTTG-3'         (SEQ ID NO: 34)

rplh
Forward:
5'-CGAAGCCTTTCTGCAGTACC-3'         (SEQ ID NO: 35)
reverse:
5'-AGGGAATCAGTCTGGGGTCT-3'         (SEQ ID NO: 36)

rpgrip1
Forward:
5'-CAGACTACCGACAGCGATGA-3'         (SEQ ID NO: 37)
Reverse:
5'-TTGGTTTCCTCAGGGACATC-3'         (SEQ ID NO: 38)
```

Immunohistological Staining and Statistical Analysis

Immunohistological staining was performed as described previously (reference documents A20, 24). The primary antibodies used in this study were as follows:
Anti-Crx (rat/polyclonal/1:200, reference document A6),
Anti-Ki67 (mouse/monoclonal/1:200/BD),
Anti-BrdU (mouse/monoclonal/1:50/BD),
Anti-active caspase-3 (rabbit/monoclonal/1:500/BD),
Anti-red/green opsin (rabbit/polyclonal/1:1000/Chemicon),
Anti-blue opsin (rabbit/polyclonal/1:500/Chemicon),
Anti-rhodopsin (RetP1; mouse/monoclonal/1:1000/SIGMA) and
Anti-Recoverin (rabbit/polyclonal/1:5000/Chemicon).

The immunoreactivity of each antibody was confirmed by immunostaining an appropriate retinal tissue as a positive control under the same conditions. Total cell counts were determined by counting nuclei stained by TOTO-3 or DAPI (Molecular Probes). Positive cells were counted in optical slice images prepared by confocal (Leica) or ApoTome (Zeiss) microscopy.

For statistical analyses, at least 2500 cells were examined in each experiment, which was performed at least 3 times. All statistical analyses were performed using GraphPad InStat version 3.0 (GraphPad Software Inc., San Diego, Calif., USA). The statistical significance of differences was determined by one-way analysis of variance (ANOVA) followed by Tukey's test for the experiments in FIG. 1$f$, by one-way ANOVA followed by Dunnett's multiple comparison test for the experiment in FIG. 3$b$, by two-way ANOVA followed by Bonferroni's test for the experiment in FIG. 1$j$-$l$. Probability values less than 5% were considered significant.

Results

In this study, the present inventors searched for inductive conditions that would promote the differentiation of retinal progenitor cells into a photoreceptor lineage. Neural retinal progenitor cells express Rx, which is essential for identification of eye field (reference documents A8, 9). Using a mouse reporter ES line having GFP knocked in at the Rx locus (W.T. and Y.S), the present inventors first purified a cell population enriched for $Rx^+$ retinal progenitor cells (FIG. 1$a$-$c$). ES cells were cultured under the SFEB/DLFA condition for 9 days, and dissociated into single cells, and the cells were sorted by FACS (FIG. 1$a$). Consistent with a previous report by the present inventors (reference document A6), on day 9, 15% of SFEB/DLFA-treated ES cells were Rx-$GFP^+$ (FIG. 1$b$). After single sorting, more than 90% of the cells were $GFP^+$ (FIG. 1$c$). In agreement with a previous report (reference document A6), immunostaining revealed that most of the sorted cells were $Rx^+$, and many of them were $Pax6^+$ (data not shown).

The present inventors next tested to determine whether or not the sorted cells would differentiate into photoreceptors in vitro. After sorting, the present inventors made re-aggregation pellets by centrifugation, and replated the pelleted cells onto a poly-D-lysine/laminin/fibronectin-coated dishes (FIG. 1$e$). After cultivation in a differentiation medium for 11 days (i.e., on differentiation day 20), a relatively small cell population (7.8±2.6%) became positive for Crx, a factor of determining the fate for the photoreceptor lineage (reference documents A10, 11) (FIG. 1$f$, lane 1). This reveals two facts. First, the purified $Rx^+$ cells have the capability of differentiating into photoreceptor precursors. Second, for these $Rx^+$ cells to achieve "efficient" differentiation into photoreceptor, certain promoting signals missing in this culture are required.

Figure 4:
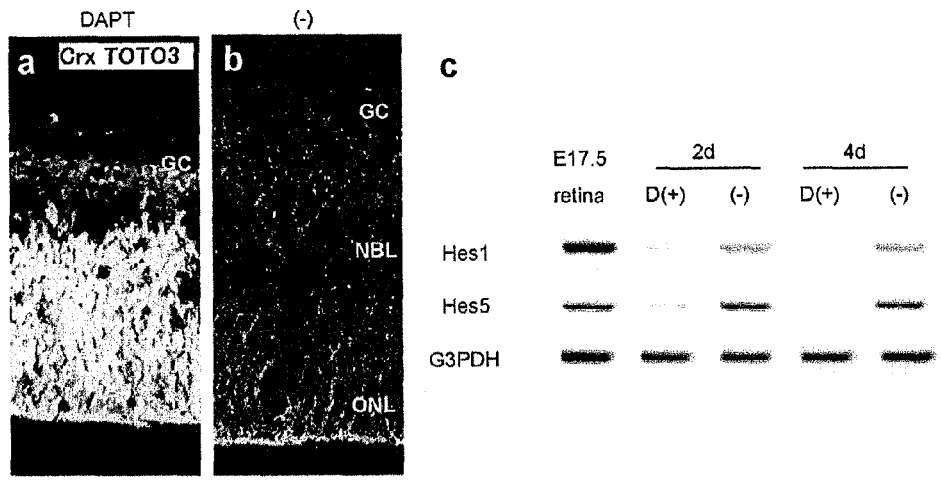
FIG. 4 The gamma secretase inhibitor DAPT promotes the differentiation of photoreceptor precursors. Retinae of E17.5 mouse were treated, or not treated, with 10 μM DAPT under tissue culture conditions for 2-4 days. (a, b) Two days later, the retinae were stained for Crx (green) and TOTO-3 (blue). Many Crx$^+$ (green) photoreceptor precursors were found in the DAPT-treated retina (a), whereas several Crx$^+$ were found in non-treated retina (b). GC, ganglion cell layer; NBL, neuroblastic layer; ONL, outer nuclear layer. (c) RT-PCR analysis of retina treated or not treated with DAPT for 2 or 4 days. It was confirmed that the expression of Hes1 and Hes5 had been decreased in the DAPT-treated retina.
Figure 5:
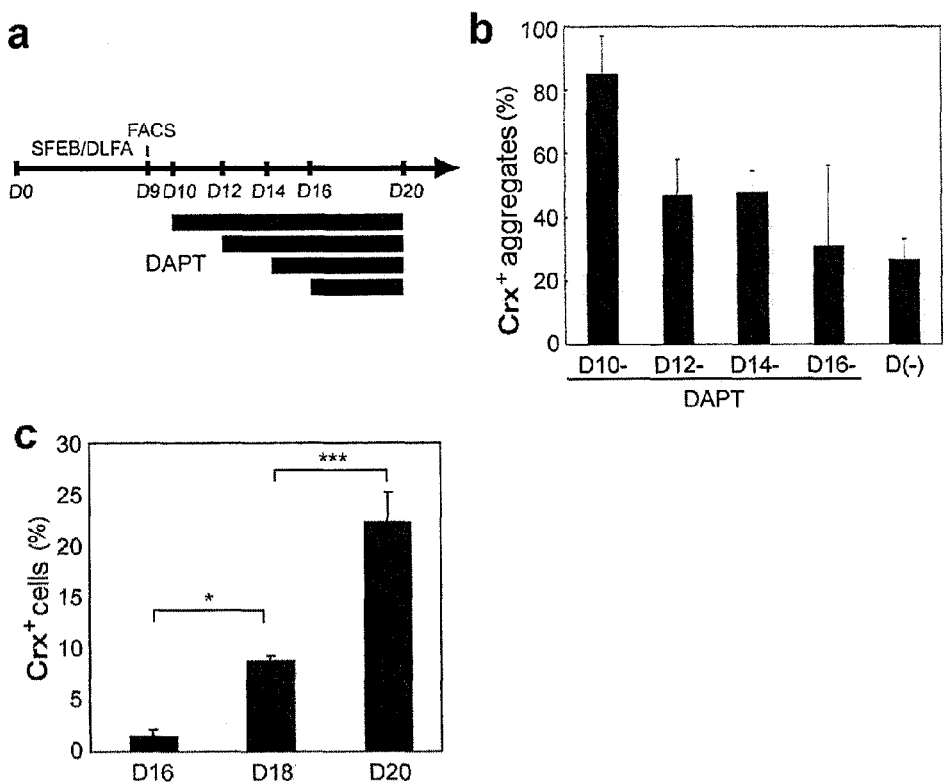
FIG. 5 DAPT promotes the differentiation of FACS-purified retinal progenitor cells into Crx$^+$ photoreceptor precursors. (a, b) Effects of DAPT treatment on the differentiation of FACS-purified, ES-derived cells into Crx$^+$ cells. (a) Culture scheme for the experiment. (b) The percentage of Crx$^+$ cells in cells treated or not treated with 10 μM DAPT on day 20. (c) The percentage of Crx$^+$ cells in FACS-purified cells treated with DAPT from day 10, on each day of differentiation (*, $P<0.05$, ***, $P<0.001$, Tukey's test).

Taking this into account, the present inventors investigated the effect of gamma secretase inhibition in this step. In a study the present inventors concurrently conducted using tissue culture, it was found that treatment of embryonic retinal tissue with the gamma secretase inhibitor DAPT (10 μM, see reference documents A15 and 16) considerably increased the ratio of $Crx^+$ photoreceptor precursors and suppressed the expression of the differentiation inhibitors Hest and Hes5 (FIG. 4). RT-PCR analysis showed that purified $Rx^+$ cells expressed Notch (Notch1-4), Hes1, Hes5 and Hey1 (FIG. 1$d$), inhibiting that Notch signaling components were present in the purified ES-derived $Rx^+$ cells. The present inventors examined the effect of Notch inhibition on these cells by treating these cells with DAPT. The cells were purified by FACS and plated as re-aggregation pellets, after which ES-derived neural retinal progenitor cells were cultured in a differentiation medium containing or not containing 10 μM DAPT (FIG. 5$a$). DAPT treatment significantly raised the frequency of $Crx^+$ cell aggregates, the DAPT treatment being most effective when applied on days 10 to 20 (FIG. 5$b$ and FIG. 1$e$). At the cellular level, under these conditions, on day 20, 22.4±2.9% of the purified Rx-$GFP^+$ cells differentiated into $Crx^+$ photoreceptor precursors (FIG. 1$f$, lane 2, FIG. 1$g$, $h$). When non-FACS-sorted ES cell-derived neural retinal progenitor cells were treated with DAPT, no evident promotion of differentiation into $Crx^+$ photoreceptor precursors was observed. By contrast, Rx-$GFP^-$ cells did not express Crx (FIG. 1$f$, lane 3). These results show that gamma secretase inhibitor promotes the in vitro differentiation of FACS-purified retinal progenitor cells into $Crx^+$ photoreceptor precursors. Therefore, efficient generation of photoreceptor precursor from ES-derived retinal progenitor cells was achieved without co-culture with embryonic retinal tissues.

Figure 11:
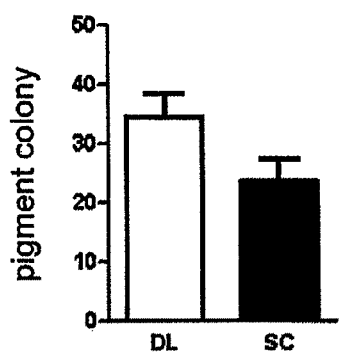
FIG. 11 Induction of differentiation of human ES cells into retinal epithelial cells by combination of Dkk-1 and Lefty-A (DL), and combination of SB-431542 and CKI-7 (SC).

Photoreceptor precursors express Crx immediately after exiting the cell cycle. Consistent with this, ES-derived $Crx^+$ cells were negative for mitosis marker Ki67 (FIG. 1$i$), demonstrating that these cells were postmitotic. The present inventors next analyzed the effects of DAPT on Ki67 expression (FIG. 1$j$) and BrdU uptake (24 hours) (FIG. 1$k$) in the purified Rx+ cells during differentiation days 11-20. On day 14 (4 days after treatment) and thereafter, the $Ki67^+$ cell population in DAPT-treated cells was smaller than that of non-treated cells (FIG. 1$j$). Likewise, on days 14-20, a fewer $BrdU^+$ cells compared with the non-treated control were observed among DAPT-treated cells. These data show that DAPT treatment reduced the number of mitotic cells in purified neural retinal progenitor cells. The present inventors investigated to determine whether the reduction in mitotic cells by DAPT was due to enhanced apoptosis (thereby excluding mitosis cells are removed) or due to an increase in the number of cells differentiating into their postmitotic state. During days 11-20, $Ki67^+$ mitosis cells were mostly not positive for active caspase 3 (apoptosis cell marker) (reference document A17). Furthermore, the proportion of cells positive for active caspase exhibited no significant difference between the DAPT-treated population and the non-treated population (on days 11, 12, 14, 16, 18 and 20, 0.17±0.04%, 0.13±0.04%, 0.10±0.07%, 0.10±0.01%, 0.13±0.02% and 0.10±0.15%, respectively) (FIG. 11). Conversely, DAPT-treated cells began to express Crx on differentiation day 16, the proportion of $Crx^+$ cells increased gradually during days 16-20 (FIG. 5$c$). These observations suggest that a gamma secretase inhibitor steers ES-derived mitotic retinal progenitor cells is toward differentiation into post-mitotic photoreceptor precursors.

Figure 2:
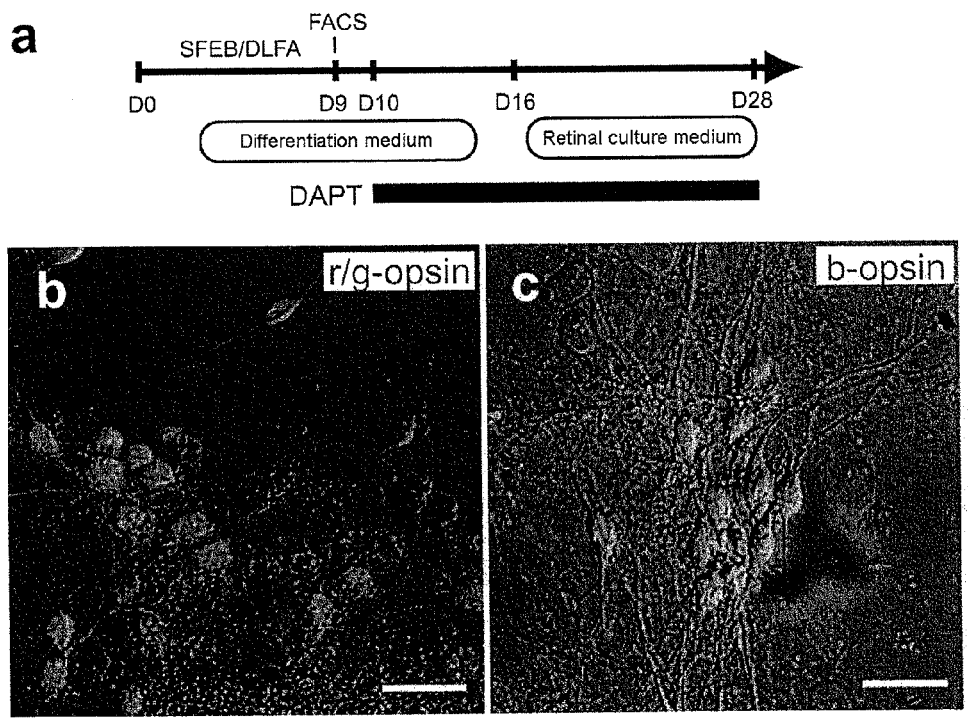
FIG. 2 Differentiation of $opsin^+$ cells from ES-derived, DAPT-induced photoreceptor precursors. (a) The procedure for differentiation of $opsin^+$ cone photoreceptors from ES cells. FACS-purified $Rx\text{-}GFP^+$ cells were cultured with DAPT for 19 days. (b, c) Merged immunostaining and Normarski images of red/green opsin (red) (b) or blue opsin (red) (c). Scale bar, 20 μm.

Next, the present inventors investigated to determine whether or not $Crx^+$ photoreceptor precursors efficiently generated using DAPT further differentiate into photoreceptors containing visual pigments. Purified ES-derived $Rx^+$ cells were cultured in a DAPT-containing differentiation medium from day 10; then on day 16 (about the time of onset of Crx expression, FIG. 2$a$), the medium was switched to a retinal differentiation medium (reference document A6). On day 28, immunolostaining showed that 11.5±2.0% and 10.7±1.6% of the ES-derived cells expressed red/green opsin and blue opsin, respectively (FIG. 2b, c); these are cone-specific pigment proteins that are indispensable for color vision. By contrast, a fewer cells (5.5±0.5%) expressed the rod type visual pigment rhodopsin (FIG. 3b, lane 2). From these findings, it is suggested that under these conditions, ES-derived $Crx^+$ photoreceptor precursors differentiate efficiently into $opsin^+$ cone type photoreceptors and less efficiently into $rhodopsin^+$ cells.

With respect to retinal degenerative diseases, in vitro generation of rod photoreceptors is particularly valuable. This is because 95% of human photoreceptors are of the rod type, and also because these cells are predominantly lost in patients with retinitis pigmentosa. To optimize conditions for rod differentiation, the present inventors next tested some soluble factors reported to have a positive effect on the genesis of rods from embryonic (or neonatal) retinal progenitor cells (reference document A18). After FACS purification and DAPT treatment, each factor was first individually added to the retina culture medium (FIG. 3a). Of the factors, acidic FGF (50 ng/ml), basic FGF (10 ng/ml), taurine (1 mM), shh (3 nM) and retinoic acid (RA, 500 nM) promoted rod differentiation (FIG. 3b, lanes 3-7; durations of treatment are shown in the Methods section). In particular, when these factors were combined, a large number of cells (17.2±1.8% of all cells) expressed rhodopsin (FIG. 3b, lane 8, FIG. 3c, d). These $rhodopsin^+$ cells co-expressed the photoreceptor marker recoverin (reference document A19) (FIG. 3e). From these findings, it was shown that a combined treatment with FGFs, taurine, shh, and RA potently promotes the differentiation of ES-derived DAPT-induced photoreceptor precursors into $rhodopsin^+/Recoverin^+$ rod photoreceptors. By contrast to $rhodopsin^+$ cells, FGFs, taurine, shh and/or RA treatment (individually or combined) did not raise the proportion of red/green $opsin^+$ cells or the ratio of blue $opsin^+$ cells; it was suggested that the response to the above-described factors might differ between somatic cone photoreceptors and somatic rod photoreceptors. Therefore, by using stepwise treatments with defined soluble factors, cone and rod photoreceptors can be efficiently and selectively generated from ES cells in vitro.

Including the present inventors' report, previous reports (reference documents A4-6) demonstrate that generation of rod photoreceptors from ES-derived progenitor cells is of low frequency unless the progenitor cells are co-cultured with retinal tissue while in its developmental stage. In a report by the present inventors (reference document A6), the present inventors examined the effects of exogeneous factors (FGFs, taurine, shh, and /RA) on SFEB/DLFA-treated cells without sorting but failed to observe obvious positive effects on rhodopsin+ photoreceptor differentiation, in contrast to their evident effect on the cells after sorting and DAPT treatment (FIG. 3b).

An important finding in this study is that FACS-purified $Rx^+$ cells is mitotic over a considerable length of period (FIG. 1j, k), raising the possibility of increasing the number of purified neural retinal progenitor cells before their use in further research. In future, this will be a major advantage of this system for transplantation research, in screening for factors that promote the differentiation and survival of photoreceptors.

Figure 6:
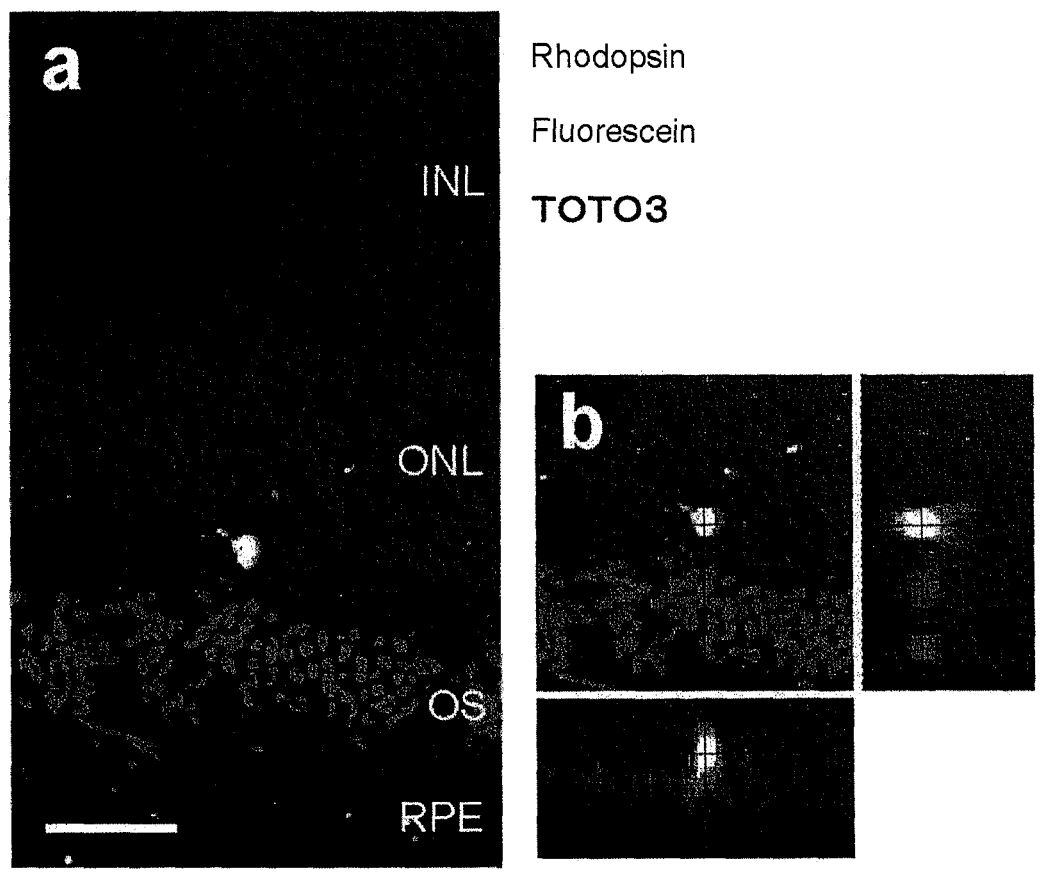
FIG. 6 In transplanted rat retina, ES-derived retinal progenitor cells survive and express rhodopsin. (a, b) FACS-purified ES-derived cells (on day 9 of differentiation) were labeled with fluorescein dye (CFSE, (5-(6)-carboxyfluorescein diacetate succinimidyl ester, Molecular Probes) for 10 minutes, and transplanted into a subretinal space in a rat eye (P21). Two weeks after the transplantation, the eyes were fixed, and stained with anti-rhodopsin (red) and anti-fluorescein (green) antibodies. The nuclei were counterstained with TOTO-3 (blue). (b) An image of reconstructed rhodopsin$^+$ cells that could be reconstituted along the Z axis. INL, inner nuclear layer; ONL, outer nuclear layer; OS, outer segment; RPE, retinal pigment epithelium. Scale bar, 20 μm.

Finally, the present study provides substantial experimental basis for applying ES cells to regenerative medicine for treatment of intractable retinal diseases. An important future goal is to rescue visual acuity by transplanting retinal (or photoreceptor) precursors into the retinae of an animal model of retinal degeneration. In a preliminary study, 2 weeks after transplantation to under the rat retina, sorted $Rx$-$GFP^+$ cells survived in the retina, expressed rhodopsin, and became integrated into the outer nuclear layer (FIG. 6a, b).

Example 2

Methods

Maintenance of Undifferentiated Monkey ES Cells

Two independent cell lines of cynomolgus monkey ES cells (CMK6 and CMK9) were maintained as described previously (reference documents B26, 28, 29). In summary, undifferentiated ES cells were maintained on a feeder layer of mitomycin C-treated mouse embryonic fibroblasts (STO cells). The STO cells were incubated with 10 μg/mL mitomycin C (Wako, Osaka, Japan) for 2 hours and plated on gelatin-coated dishes. The undifferentiated monkey ES cells were incubated in a DMEM/F-12 (Sigma, St. Louis, Mo.) supplemented with 0.1 mM 2-mercaptoethanol (Sigma), 0.1 mM non-essential amino acids (Sigma), 2 mM L-glutamine (Sigma), 20% knockout serum replacement (KSR; Lot.1139720 and 1219101, GIBCO), 1,000 units/ml leukemia inhibitor (ESGRO; Chemicon, Temecula, Calif.) and 4 ng/ml basic fibroblast growth factor (Upstate Biotechnology, Lake Placid, N.Y.). ES cells were passaged every 3 days using 0.25% trypsin (GIBCO) in PBS supplemented with 1 mM $CaCl_2$ and 20% KSR. The monkey ES cell lines used in this study formed colonies tightly packed with each cell showing a high nuclear/cytoplasmic ratio. These cells expressed markers of undifferentiated ES cells such as Oct-3/4 (reference document B30) and Nanog (reference documents B31, 32), but did not express pan-neural markers such as nestin, βIII-tubulin and microtubule-related protein-2(a+b) even when continued to be cultured for 1 year or more. Therefore, these ES cells remained undifferentiated during the culture by the present inventors.

Differentiation of Monkey ES Cells into Retinal Cells

ES colonies were partially dissociated with 0.25% trypsin (in a PBS containing 1 mM $CaCl_2$ and 20% KSR) into clumps (5 to 10 cells per clump). It is noticeable that when this clumps of ES cells were too large (for example, exceeding 50 cells per aggregate), the neural induction efficiency declined. When ES cells dispersed to single cells were used, the cell viability declined, and retinal cells could not efficiently be induced. ES clumps were incubated on a gelatin-coated dish for 30 minutes, whereby STO feeders were removed. ES clumps were plated on a dish of bacterial grade using an ES differentiation medium at a density of $6.7×10^3$ aggregate per ml. The composition of the differentiation medium was as follows. [G-MEM (GIBCO), 10% KSR, Lot.1139720 and 1219101, 0.1 mM non-essential amino acids, 1 mM pyruvate and 0.1 mM 2-mercaptoethanol]. Recombinant Dkk-1 protein (100 ng/ml) and Lefty-A protein (500 ng/ml; R&D Systems, Minneapolis, Minn.) were added to the differentiation medium of suspension culture for 18 days. Thereafter, spontaneously formed ES cell aggregates were combined, and were plated on a poly-D-lysine/laminin/fibronectin-coated 8-well culture slide at a density of 20 to 15 aggregates per $cm^2$.

To generate photoreceptors, SFEB/DL-treated, differentiated cells were further incubated with RA/T/N2 medium (GMEM+5% KSR+N2 supplement (GIBCO)+retinoic acid (1 μM, Sigma)+taurine (100 μM, Sigma)+penicillin (100 units/ml)/streptomycin (100 μg/ml)) for at least 30 days.

Maintenance of Undifferentiated Human ES Cells

Human ES cells were supplied by N. Nakatsuji and H. Suemori (Kyoto University), and used in compliance with the Human ES cell Guidelines of the Japanese government. These independent human ES cell lines (khES-1, khES-2, and khES-3) were maintained as described previously (reference document B33). In summary, undifferentiated human ES cells were maintained on a feeder layer of mitomycin C-treated mouse embryonic fibroblasts (Oriental Yeast, Tokyo, Japan). Human ES cells were maintained in DMEM/F-12 supplemented with 0.1 mM 2-mercaptoethanol, 0.1 mM non-essential amino acids, 2 mM L-glutamine, 20% KSR (Lot.1219101) and 4 ng/ml basic fibroblast growth factor (Upstate Biotechnology) in a humidified atmosphere of 2% $CO_2$ and 98% air at 37° C. ES cells were passaged with 0.25% trypsin and 0.1 mg/ml collagenase IV (GIBCO) (in a PBS containing 1 mM $CaCl_2$ and 20% KSR) every 3 to 4 days. These human ES cell lines expressed the undifferentiated ES cell markers Oct-3/4 and Nanog. These human ES cells were immunonegative for pan-neural markers such as nestin, βIII-tubulin and microtubule-associated protein-2 (a+b); consistent with human ES cells remaining undifferentiated in the cultivation of the present inventors.

Differentiation of Human ES Cells into Retinal Cells

ES colonies were treated with 0.25% trypsin and 0.1 mg/ml collagenase IV (in a PBS containing 1 mM $CaCl_2$ and 20% KSR (Lot. 1219101)), and then gently disassembled for partial dissociation to obtain clumps (5 to 10 cells per clump). In 20% KSR-containing ES differentiation medium [G-MEM, 0.1 mM non-essential amino acids, 1 mM pyruvate and 0.1 mM 2-mercaptoethanol], at a density of $6.7 \times 10^3$ ES clumps per ml, ES clumps were plated onto a gelatin-coated dish for 1 day. After suspension culture for 1 day, floating ES aggregates were incubated in an ES differentiation medium containing 20% KSR on a dish of bacterial grade for 4 days, then in an ES differentiation medium containing 15% KSR for 8 days, and thereafter in an ES differentiation medium containing 10% KSR for 6 days. During suspension culture for 20 days, Dkk-1 (100 ng/ml) and Lefty-A (500 ng/ml) were added to the differentiation medium. ES cell aggregates were then replated en bloc onto poly-D-lysine/laminin/fibronectin-coated culture slides at a density of 10 to 20 aggregates per $cm^2$. In adhesion culture, the cells were incubated in an ES differentiation medium containing 10% KSR.

To generate photoreceptors, SFEB/DL-treated ES cells were incubated in RA/T/N2 medium (GMEM+5% KSR+ retinoic acid (1 μM)+taurine (100 μM)+N2 supplement+ penicillin (100 units/ml)/streptomycin (100 μg/ml)) for at least 30 days. The medium was replaced with a fresh supply every two days. Although the differentiation efficiency varied depending on the cell line, it was confirmed that in three independent human ES cells (khES1, khES2 and khES3), this method induced differentiation into retinal cells.

Immunocytochemistry

Cells were fixed with 4% para-formaldehyde, and immunolabeled as described previously (reference documents B9, 33, 34).

The primary antibodies and their working dilutions were as follows:

Mouse anti-βIII tubulin (1:500, Sigma)
Rat anti-Crx (1:200) (reference document B9)
Mouse anti-microtubule-associated protein-2(a+b) (1:500, Sigma)
Mouse anti-Mitf (1:30, abcam)
Rabbit anti-Nanog (1:1000, ReproCELL)
Rabbit anti-nestin (1:1000, Covance)
Mouse anti-Oct3/4 (1:200, BD pharmingen)
Rabbit anti-Pax6 (1:600, Covance)
Mouse anti-Pax6 (1:200, DSHB)
Anti-PKC (sigma)
Rabbit anti-Recoverin (1:3000, chemicon)
Mouse anti-rhodopsin (RET-P1, 1:2000, Sigma)
Rabbit anti-RPE65 (1:1000)
Rabbit anti-Rx (1:200) (reference document B9)
Rabbit anti-ZO-1 (1:100, Zymed)

The secondary antibodies used were as follows:

An anti-mouse IgG antibody, anti-rabbit IgG antibody, anti-rat IgG antibody (1:200, Jackson Immunoresearch Laboratories, West Grove, Pa.), each conjugated with Cy3 or FITC. F-actin was stained with Alexa488-conjugated phalloidin (Molecular Probes). Cell nuclei were counterstained with 4',6-diamidino-2-phenylindol (DAPI, 1 μg/ml, Molecular Probes) or TOTO-3 (Molecular Probes). The labeled cells were imaged using laser scanning confocal microscopy (Leica) and ApoTome (Zeiss).

Electron Microscopic Analysis

Cells were fixed with 2% glutaraldehyde/0.1M PB for 10 minutes, and post-fixed with 1% osmium oxide (0.1M PB, pH 7.3), and treated with a ethanol series (50%, 60%, 70%, 80%, 90%, 99.5% and 100%) for dehydration, and embedded in epoxy resin. Ultrathin sections were cut from these samples using an ultramicrotome, and stained with uranyl acetate and lead citrate, and then visualized by electron microscopy.

RT-PCR

In the same manner as Example 1, the expression of the following human genes was examined by RT-PCR analysis. The primers used are as follows:

```
Transducin alpha 1
(Guanine nucleotide-binding protein alpha 1
subunit (GNAT1))
Forward:
5'-CATCGAGACGCAGTTCTCCT-3'       (SEQ ID NO: 39)
Reverse:
5'-AGTAGCGGTGGTTGCAGATG-3'       (SEQ ID NO: 40)

Phosducin (PDC)
Forward:
5'-TCAAAGGAACGAGTCAGCAG-3'       (SEQ ID NO: 41)
Reverse:
5'-CTGCTGCAAGGCATGTTAAA-3'       (SEQ ID NO: 42)

Phosphodiesterase 6b (PDE6b)
Forward:
5'-CAGTGATGAACACCGACACC-3'       (SEQ ID NO: 43)
Reverse:
5'-ATTTGACCAGGTCCAGTTCG-3'       (SEQ ID NO: 44)

PDE6c
Forward:
5'-CTGAGGTGGCCTCTAGGTTG-3'       (SEQ ID NO: 45)
Reverse:
5'-GCTGGTGTGATGAAGCCTTAG-3'      (SEQ ID NO: 46)

cGMP-gated channel alpha1
(CNGA1)
Forward:
5'-GATCCCTCGGGAAACACATA-3'       (SEQ ID NO: 47)
Reverse:
5'-CGAGAGAACCGTAACAACCTGG-3'     (SEQ ID NO: 48)

Rhodopsin kinase (GRK1)
Forward:
5'-GGACTGGTTCCTGGACTTCA-3'       (SEQ ID NO: 49)
Reverse:
5'-AAGCCAGGGTTCTCCTCATT-3'       (SEQ ID NO: 50)

Arrestin (S-antigen, SAG)
Forward:
5'-GGTGTTGTCCTGGTTGATCC-3'       (SEQ ID NO: 51)
```

```
-continued
Reverse:
5'-TCAGCGTCTTGGTCAAAGTG-3'       (SEQ ID NO: 52)

Arrestin 3 (ARR3)
Forward:
5'-GGTGTTGTCCTGGTTGATCC-3'       (SEQ ID NO: 53)
Reverse:
5'-GTCACAGAACAGGGCAGGTT-3'       (SEQ ID NO: 54)

Retinol dehydrogenase 12
(RDH12)
Forward:
G5'-CTTCTCCCCCTTTTCAAGA-3'       (SEQ ID NO: 55)
Reverse:
5'-CTTTAGGGTTGGCCTTCTCC-3'       (SEQ ID NO: 56)

Glyceraldehyde-3-phosphate
dehydrogenase (GAPDH)
Forward:
5'-GCCTCTACGTTGCTGGATGT-3'       (SEQ ID NO: 57)
Reverse:
5'-GCTGGTGTGATGAAGCCTTAG-3'      (SEQ ID NO: 58)
```

Statistic Analysis

Values are expressed as means±S.E.M. For statistic analysis, 100 to 200 colonies in each experiment were examined, each experiment being performed at least 3 times. All statistical analyses were performed using GraphPad InStat version 3.0 (GraphPad Software Inc., San Diego, Calif., USA). For the experiments in FIG. 7b, statistical significance of difference was determined by one-way analysis of variance (ANOVA) followed by Dunnet's test. The data obtained from FIG. 8a, d, e, h and i were evaluated by unpaired t-test. A probability values less than 5% were judged to indicate a significant difference.

Results

Figure 7:
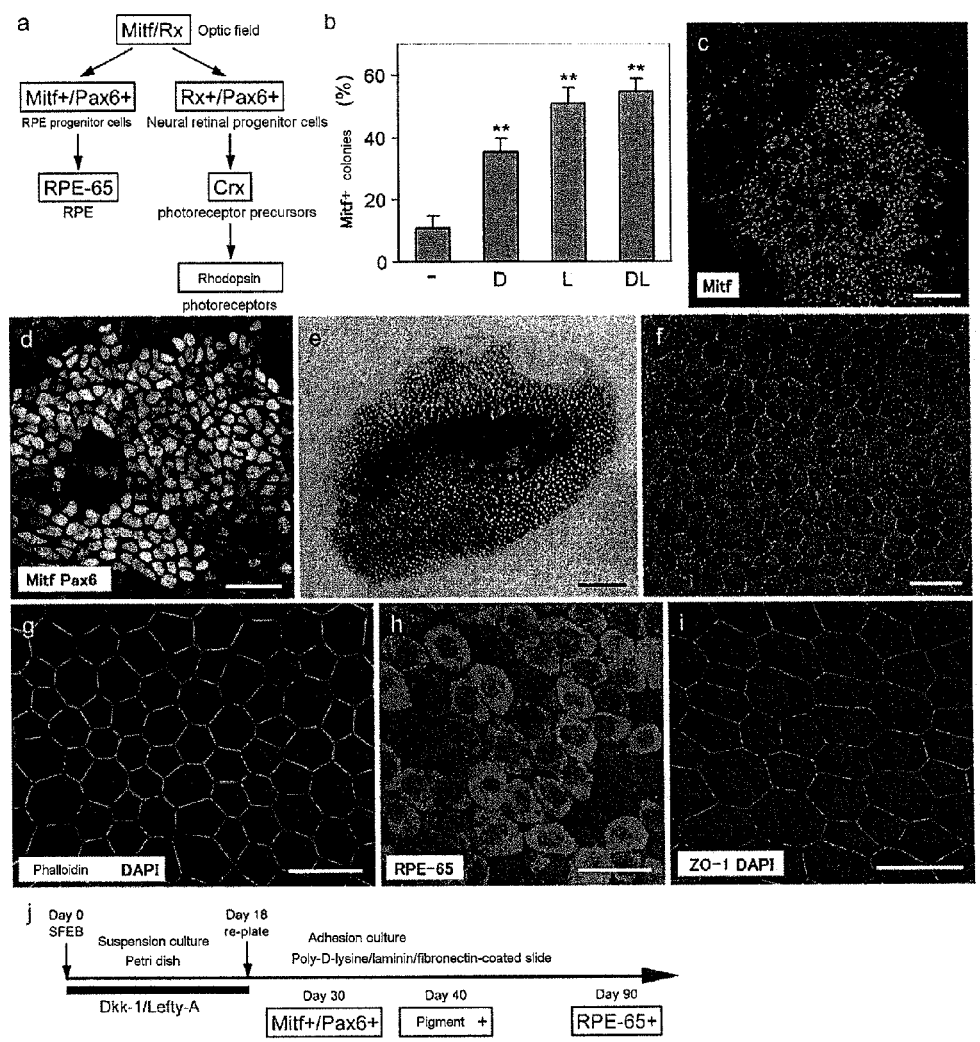
FIG. 7 Directed differentiation of RPE cells from monkey ES cells when the ES cells were cultured without containing serum and feeders. (a) Multiple step commitment in the development of retinal cells. Markers for respective differentiation steps are shown in windows. (b) The ratio of Mitf$^+$ colonies in SFEB-treated ES cells. When SFEB culture was combined with Dkk-1 and Lefty-A, the differentiation of Mitf$^+$ colonies was most efficiently induced. ** $P<0.01$, compared with SFEB alone. (c) SFEB/DL-treated monkey ES cells differentiate into Mitc cells. (d) Production of Mitf$^+$/Pax6$^+$ RPE progenitor cells from monkey ES cells. (e) A phase contrast image of pigment cells that have differentiated from monkey ES cells (on day 40). (f) A highly magnified image of monkey ES cell-derived RPE cells in SFEB/DL culture. It is seen that the pigmented cells exhibit a polygonal shape. (g) Phalloidin staining revealed the polygonal shape of RPE cells. (h) Monkey ES cell-derived pigment cells express RPE-65, a protein specific for mature RPE. (i) Formation of tight junctions was determined by immunological staining with anti-ZO-1 antibody. (j) A schematic diagram of RPE differentiation in SFEB/DL culture. Scale bars, 100 μm (c, e), 30 μm (d), 20 μm (f, g, h, i).

First, the SFEB (serum-free floating culture of embryoid body-like aggregates) method was improved, and in the same manner as with mouse ES cells, whether or not retinal progenitor cells were produced from monkey ES cells was examined (reference documents B9, 11). The monkey ES cells were dissociated to small clumps of 5 to 10 cells, seeded in Petri dish, and suspension-cultured in a differentiation medium (see the "Methods" section). Under these conditions, monkey ES cells formed embryoid body-like aggregates. On day 18, these aggregates were placed onto poly-D-lysine/laminin/fibronectin-coated slides. In the vertebral animals, the optic vesicle devolves into the neural retina (inner layer) and retinal pigment epithelium (RPE, outer layer). Whereas neural retinal progenitor cells express Rx (reference documents B8, 12, 13), presumptive RPE expresses Mitf (reference documents B9, 14-16) (FIG. 7a). Therefore, whether or not the SFEB-treated ES cells expressed these two markers was examined. After 40 days in SFEB culture, immunostaining revealed that only a few colonies were Mitf-positive (to 10%, FIG. 7b). To identify culture conditions that efficiently induce the formation of Mite cells from mouse ES cells, the effects of soluble factors on the number of Mite colonies in SFEB culture were examined. The Wnt antagonist Dkk-1 and the nodal antagonist Lefty-A both promote differentiation from mouse ES cells to Rx$^+$ retinal progenitor cells (reference document B9). When mouse ES cells were treated with Dkk-1 (100 ng/ml) or Lefty-A (500 ng/ml), the ratio of Mitf$^+$ colonies increased to 35.3±4.4% and 50.8±5.0%, respectively (FIG. 7b). When mouse ES cells were cultured with the addition of both Dkk-1 and Lefty-A for 16 days (hereinafter, referred to as SFEB/DL culture), a slight improvement exceeding the results from administration of Lefty-A alone was observed (54.6±4.2% of all colonies, FIG. 7b, c). Mitf$^+$ cells induced by SFEB/DL culture co-expressed Pax6 (90%, FIG. 7d). This result agrees with the profile of an in vivo marker of embryo RPE (reference documents B9, 14-16).

In SFEB/DL culture of monkey ES cells, on day 40, pigmented cells were observed under light microscope (FIG. 7e). After that, these cells accumulated more pigmentation, and adopted a polygonal morphology with a squamous appearance (FIG. 7f). F actin staining using phalloidin revealed that in these pigmented cells, polygonal actin bundles characteristic of RPE (reference document B17) were formed (FIG. 7g). On day 90, pigmented cells expressed the mature RPE marker RPE-65 (FIG. 7h), and expressed the tight junction marker ZO-1 (FIG. 7i). From these results, the present inventors conclude that monkey ES cell-derived pigment cells have typical features of mature RPE.

Figure 8:
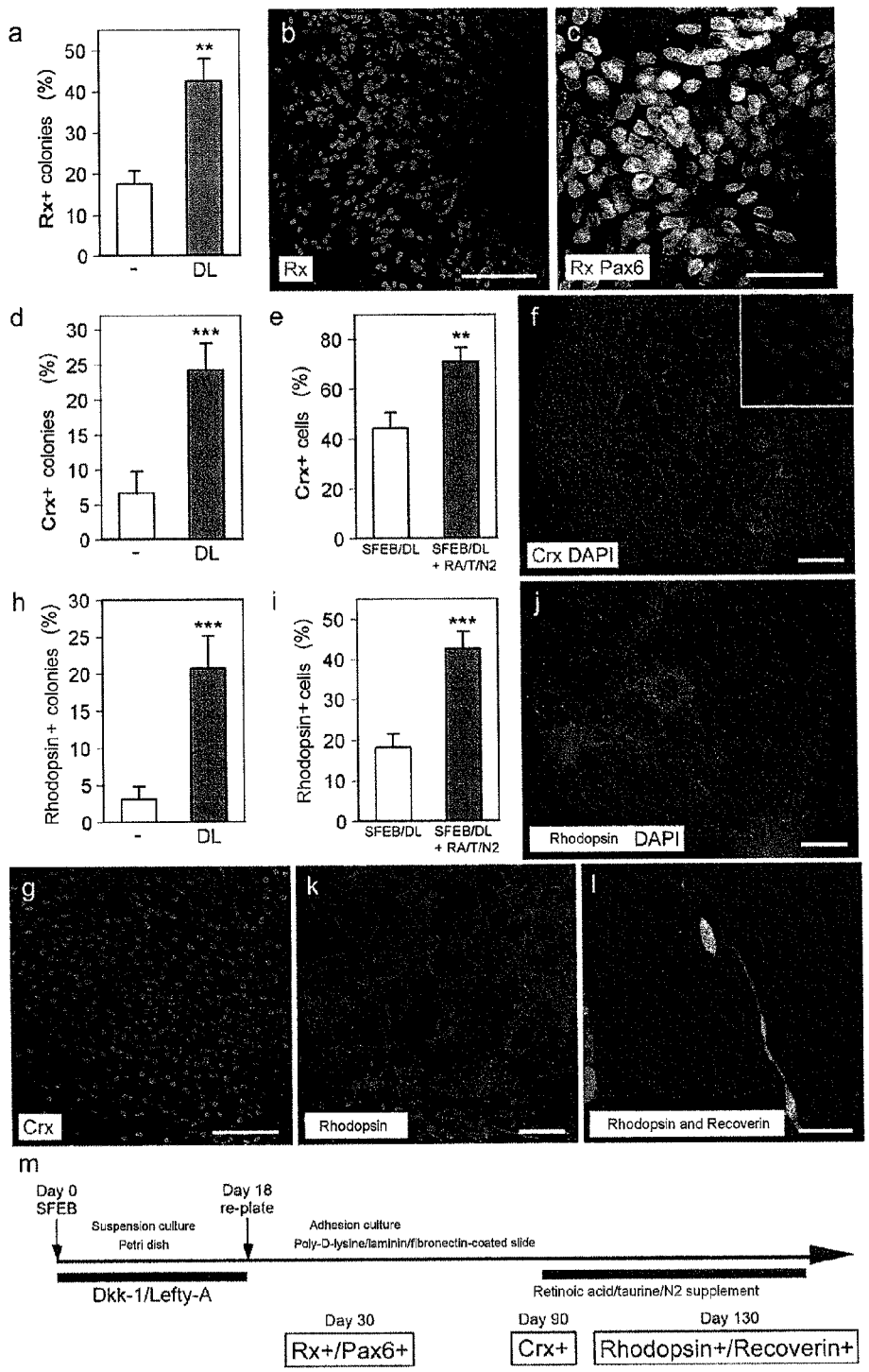
FIG. 8 Retinoic acid, taurine and N2 supplement promote differentiation into photoreceptors. (a) Dkk-1 and Lefty-A increase the ratio of Rx$^+$ colonies in SFEB culture.  $P<0.01$, comparison versus SFEB alone. (b) In SFEB/DL-treated ES cells, Rx$^+$ cells are efficiently induced. (c) Production of Rx$^+$/Pax6$^+$ neural retinal progenitor cells from monkey ES cells. (d) SFEB/DL treatment increases the ratio of Crx$^+$ colonies. * $P<0.01$, compared with SFEB alone. (e) RA/T/N2 treatment increases the ratio of Crx$^+$ cells.  $P<0.01$, comparison versus SFEB/DL alone. (f, g) Efficient differentiation of Crx$^+$ photoreceptor precursors from monkey ES cells. (h) SFEB/DL treatment increases the ratio of rhodopsin$^+$ colonies. * $P<0.01$, compared with SFEB alone. (i) RA/T/N2 treatment increases the ratio of rhodopsin$^+$ cells. *** $P<0.01$, compared with SFEB/DL alone. (j, k) Efficient differentiation of rhodopsin$^+$ photoreceptors from monkey ES cells. (l) Rhodopsin$^+$ cells co-express Recoverin. (m) A schematic diagram of photoreceptor differentiation in SFEB/DL and RA/T/N2 culture. Scale bars, 100 μm (b, f, j, g), 30 μm (c, k), 20 μm (l).

Next, generation of neural retinal progenitor cells from monkey ES cells under SFEB/DL conditions was examined. On day 30 of culture, 42.5±5.4% of the SFEB/DL-treated colonies expressed Rx. Meanwhile, 17.5±3.1% of the SFEB-treated colonies were immuno-positive for Rx (FIG. 8a, b). The Rx$^+$ cells in SFEB/DL culture were mostly Pax6$^+$ (FIG. 8c). This agrees with the marker profile of neural retinal progenitor cells. The induced Rx$^+$ cells were often observed in close proximity to Mitf$^+$ cell cluster. Similar observations were obtained for the induced mouse ES cells (reference document B9). SFEB/DL treatment induces the differentiation of primate ES cells into cells having features of retinal progenitor cells.

Subsequently, in vitro differentiation of monkey ES cells into photoreceptors was examined. In the embryo, during the retina developmental process, photoreceptor precursors express Crx (reference documents B18, 19). After 90 days of SFEB culture, only 6.7±3.1% of colonies expressed Crx (FIG. 8d). By contrast, SFEB/DL treatment generated more Crx$^+$ colonies (24.2±3.8%, FIG. 8d). Because retinoic acid and taurine promote photoreceptor differentiation (reference documents B20-23), whether these factors enhance the production of photoreceptors even in these SFEB/DL cultures was examined. On day 90 and after, SFEB/DL-treated ES cells were incubated in medium containing RA (1 μM), taurine (100 μM) and N2 supplement (RA/T/N2 medium). On day 130, in SFEB/DL+RA/T/N2 supplement, 28.5±3.6% of colonies were Crx-positive. Strikingly, 71.0±5.4% of the cells in the Crx$^+$ colonies expressed Crx by day 130; by contrast, in the absence of RA/T/N2 supplement, 43.2±6.3% were Crx$^+$ (FIG. 8e, f, g). Strong induction of the expression of Crx$^+$ like this has not been reported for other ES cell differentiation systems.

To determine whether or not monkey ES cells are capable of differentiating into mature photoreceptors, the expression of the photoreceptor marker rhodopsin was examined in SFEB/DL culture. On day 130 of SFEB/DL culture, rhodopsin-positive cells were evidently present in these cultures, but in the case of SFEB culture, they were only rarely observed (FIG. 8h). With RA/T/N2 treatment, the ratio of rhodopsin$^+$ cells in SFEB/DL-treated culture increased remarkably (FIG. 8i, j, k). These rhodopsin$^+$ cells co-expressed Recoverin, a marker for photoreceptor and cone bipolar cells (reference document B24, FIG. 8l). In addition to photoreceptors, under these culture conditions, other retinal neurons (PKC$^+$ bipolar cells, HPC$^+$/Pax6$^+$ amacrine cells, and glutamine synthase$^+$ Muller cells were also observed (data not shown). For two independent ES cell lines (CMK6, CMK9; ordinary karyotypes), similar results were obtained (data not shown). From these results, it is concluded that SFEB/DL+RA/T/N2 treatment efficiently generates photoreceptors from monkey ES cells.

Finally, whether human ES cells are capable of differentiating into retinal cells was examined. By modifying the treatment conditions from some viewpoints, SFEB/DL culture for human ES cells was optimized (see "Methods" section). In the same manner as the method established for monkey ES cell culture (FIG. 7*j*, 2*m*), human ES cells were dissociated to cell clumps (5 to 10 cells per clump), the Wnt antagonist Dkk-1 (100 ng/ml) and the nodal antagonist Lefty-A (500 ng/ml) were applied for the first 20 days of suspension culture. Next, ES cell aggregates were replated onto a poly-D-lysine/laminin/fibronectin-coated slide. Under these conditions, 73.8±5.5% of the colonies were nestin-positive. This does not disagree with the fact that SFEB/DL treatment induces the neural differentiation of human ES cells in the same manner as with monkey cells.

Figure 9:
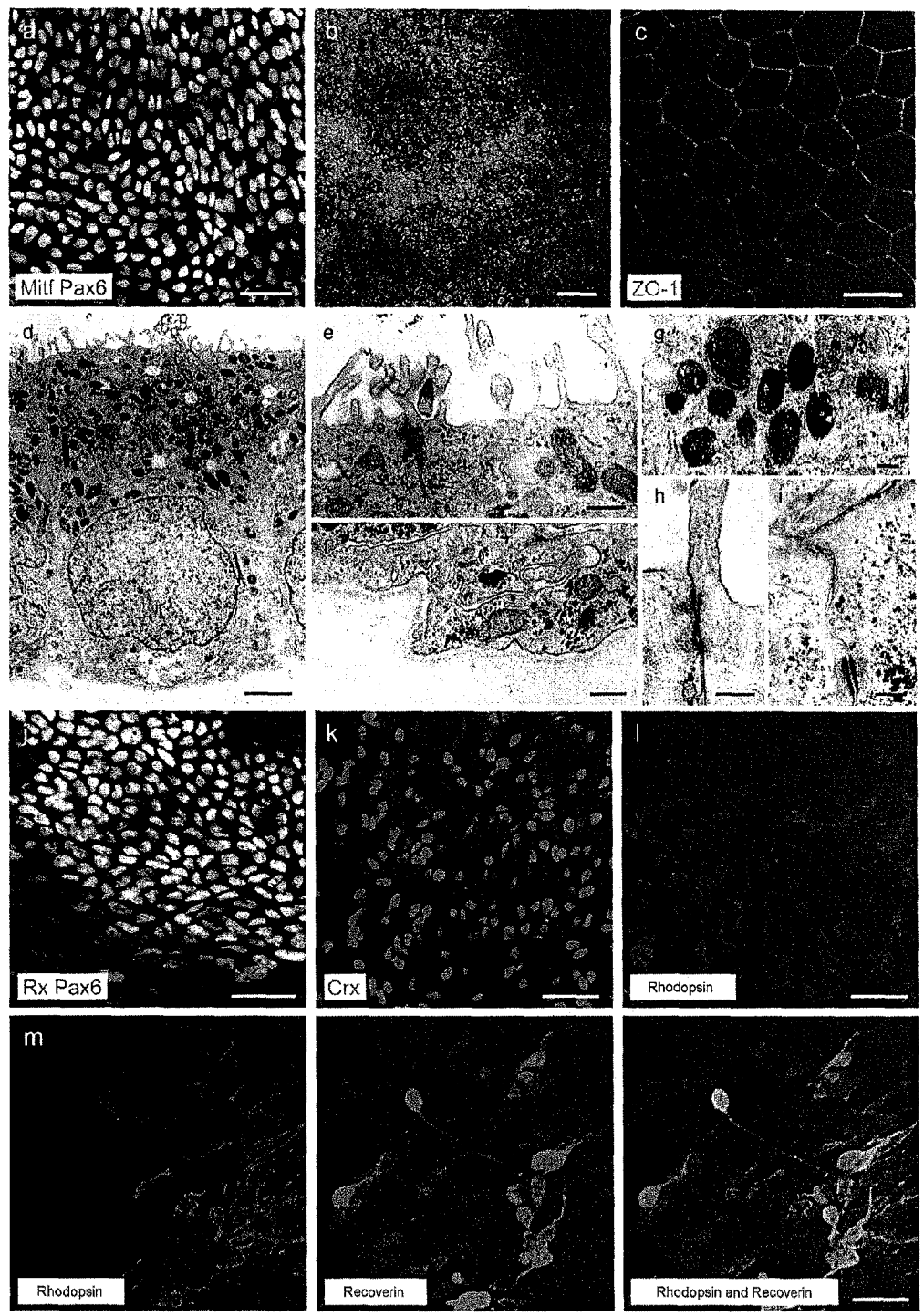
FIG. 9 Production of RPE cells and photoreceptors from human ES cells. (a-i) Human ES cells differentiate efficiently into RPE cells. (a) SFEB/DL-treated human ES cells differentiate efficiently into Mitf$^+$/Pax6$^+$ RPE progenitor cells. (b) Efficient production of pigment cells from human ES cells as determined by phase-contrast microscopy. (c) The hexagonal shape and tight junctions of these cells are clarified by immunostaining with anti-ZO-1 antibody. (d-i) Electron microscopic analysis of human ES cell-derived RPE cells. (d) SFEB/DL-treated human ES cells had features characteristic of RPE. Human ES cell-derived pigment cells had microvilli (e), a basal membrane (f), melanin granules (g), adherens junctions and tight junctions (h, i). (j-m) Differentiation of photoreceptors from human ES cells treated with SFEB/DL and RA/T/N2. (j) Human ES cells differentiate into Rx$^+$/Pax6$^+$ neural retinal progenitor cells. (k-m) Production of Crx$^+$ photoreceptor precursors (k) and rhodopsin$^+$ photoreceptors (l) from SFEB/DL cultured and RA/T/N2-treated human ES cells. (m) Human ES cell-derived rhodopsin$^+$ cells co-express Recoverin. Scale bars, 30 μm (a, j, k, l), 50 μm (b), 2 μm (d), 500 nm (e, f), 200 nm (g, h, i), 20 μm (m).
Figure 12:
FIG. 12 SFEB/DL-induced pigment cells that have phagocytized latex beads. Each arrowhead indicates a latex bead.

Differentiation of RPE cells was also examined. On day 50, Mitf$^+$/Pax6 colonies had been abundantly produced (30.6±4.7% of the colonies, FIG. 9*a*). In these SFEB/DL-treated human ES cultures, on day 60, pigment cells exhibiting a squamous, hexagonal morphology were abundantly present (FIG. 9*b*). Immunostaining using anti-ZO-1 antibody revealed that human ES cell-derived pigment cells formed tight junctions by day 120 (FIG. 9*c*). To determine whether or not the pigmented cells induced by SFEB/DL have the structural characteristics of RPE, electron photomicrographs of these cells were examined. ES-derived pigmented cells were polarized with apical microvilli and basement membrane (FIG. 9*d, e, f*). Melanin granules were abundant in the cytoplasm, predominantly in the apical and mid-portions of the cells, but they were not contained in the bottom cytoplasm (FIG. 9*d*). These are characteristics of mature human RPE (reference document B25). Melanin granules of different maturity were present in these ES cell-derived pigmented cells (FIG. 9*g*). The presence of tight junctions and adherens junctions linkage was confirmed by electron microscopy (FIG. 9*h, i*). Phagocytosis is an important function of RPE, and is indispensable for the maintenance of the photoreceptor function. Hence, the present inventors conducted latex beads phagocytosis assay to determine the phogocytotic activity of human ES-derived pigmented cells. Electron microscopy revealed pigmented cells taking latex beads, induced by SFEB/DL (FIG. 12). From these findings, it is concluded that human ES cells differentiate into cells having typical features of RPE in SFEB/DL culture.

Figure 13:
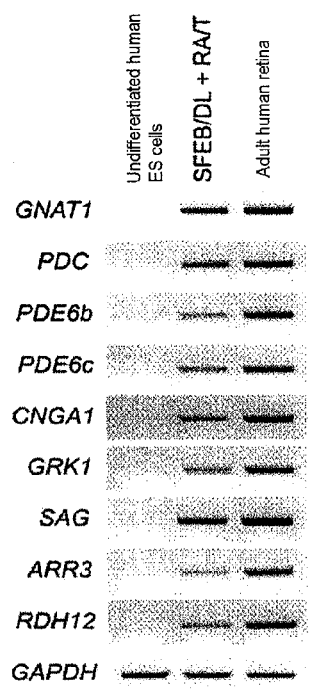
FIG. 13 Expression of photoconduction gene in human ES cells treated with SFEB/DL and RA/T/N2. Adult human retinal cDNA (BD Bioscience Clontech) was used as a positive control. GNAT1: guaninenucleotide-binding protein alpha 1, PDC: phosducin, PDE: phosphodiesterase, CNGA1: cyclin nucleotide gated channel alpha 1, GRK: rhodopsin kinase, SAG: S antigen, ARR3: arrestin 3, RDH: retinol dehydrogenase, GAPDH: glyceraldehyde-triphosphate dehydrogenase.

Next, whether capable of differentiating into photoreceptors by subsequently treating with SFEB/DL+RA/T/N2 was examined. Whether or not Rx$^+$/Pax6$^+$ neural retinal progenitor cells were produced from SFEB/DL-cultured human ES cells was examined. On day 50, 13.1±2.3% of the colonies were Rx$^+$/Pax6$^+$ (FIG. 9*j*). That is, SFEB/DL treatment promotes the differentiation of human ES cells into neural retinal progenitor cells. To determine whether the retinal progenitor cells induced by SFEB/DL treatment would differentiate into photoreceptors, the cells were treated with RA/T/N2 on day 120. On day 90, Crx$^+$ photoreceptor precursor were observed; on day 170, the aforementioned photoreceptor precursors accounted for 20.0±3.5% of the entire colony count (FIG. 9*k*). Rhodopsin$^+$ rod photoreceptors emerged by day 130; on day 200, 14.3%±4.2 of the colonies were rhodopsin-positive (FIG. 9*l*). These rhodopsin$^+$ cells co-expressed Recoverin (FIG. 9*m*). Also observed were red/green opsin+ (21.4±4.0% of all colonies) or blue opsin$^+$ cone photoreceptors (23.9±3.7% of all colonies). Furthermore, the present inventors examined the expression of genes responsible for photoconduction in rods and/or cones by RT-PCR analysis. Cells treated with SFEB/DL and RA/T/N2 were expressing transducin-alpha (rods), phosducin (rods and cones), phosphodiesterase (6b: rods, 6c: cones), cyclin nucleotide-gated channel (a1: rods), rhodopsin kinase (grk-1: rods), arrestin S antigen (rods) arrestin 3 (cones) and retinol dehydrogenase (rods and cones) on days 140 to 200 (FIG. 13). These results suggest that human ES cell-derived photoreceptor have functional constituents for photoreactions. It was concluded that when treated with SFEB/DL, human ES cells efficiently generate retinal progenitor cells, and that retinal progenitor cells differentiate into photoreceptors under RA/T/N2 culture conditions.

Human ES cells cultured on mouse feeder cells express an immunogenic non-human sialic acid on the surface thereof (reference document B27). These xenogenic factors may cause graft rejection by the immune system following transplantation. Therefore, it is essential for the clinical application of these transplantation strategies to generate cells differentiated from human ES cells without contamination of substances derived from any other animal. In previous study, retinal progenitor cells were induced in the presence of fetal calf serum (reference document B9). Furthermore, Lamba et al. generated retinal progenitor cells from human ES cells using Matrigel (a mouse sarcoma-derived material, not completely characterized, and may contain zenogenic components (reference document B10)). No cases have been reported on differentiation into photoreceptors using a defined culture (culture with synthetic medium). In this regard, the method of producing retinal cells described herein decisively differs from any previous reports. This culture technique allows the obtainment of a considerable amount of retinal cells based on human ES cells, and uses well-defined substances only.

Comprehensive functional analysis and transplantation research on these ES cell-derived retinal cells have two drawbacks: (1) A sorting system for pure photoreceptors, RPE cells or progenitor cells, and (2) long cultivation of the resulting mature retinal cells. However, because Example 1 showed that a gamma secretase inhibitor dramatically promoted photoreceptor differentiation in FACS-purified mouse ES cell-derived Rx$^+$ cells, these problems will be solved in the future. Radtke et al. demonstrated that transplantation of both neural retinal tissue and RPE tissue ameliorates the vision of patients with retinitis pigmentosa (reference document B4). Hence, transplanting a human ES cell-derived photoreceptor and an RPE cell in combination could be a more effective therapeutic strategy. Because the efficacy and safety of transplantation therapy are deemed the most important, it is essential to investigate these approaches fully in corresponding animal models. Because the culture system presented herein is effective on both monkey and human ES cells, the system must be helpful for homogenous transplantation experiment in monkeys using monkey ES cell-derived photoreceptors and RPE cells. Furthermore, this differentiation system and the human ES cell-derived cells obtained may contribute to the promotion of the adductive development of therapeutic drugs and to increased understanding of the development of the human central nervous system (particularly the eye).

Example 3

Mouse ES cells were cultured in the presence of SB-431542 (0.1 to 10 μM) and/or CKI-7 (1 to 100 μM) under SFEB conditions. Five days after the start of the culture, the cells were recovered and re-suspended in a fresh differentiation medium, and, to produce re-aggregated pellets, the suspension was centrifuged at 800 g for 10 minutes. After cultivation at 37° C. for 1 hour, three to five re-aggregated pellets per cm$^2$ were replated onto poly-D-lysine/laminin/fibronectin-coated culture slides, along with differentiation medium. After cultivation for 5 days, the cells were fixed and stained with anti-βII tubulin antibody, and the ratio of βII tubulin-positive cells was determined under microscopy. The other experimental conditions were the same as those for Example 1.

Figure 10:
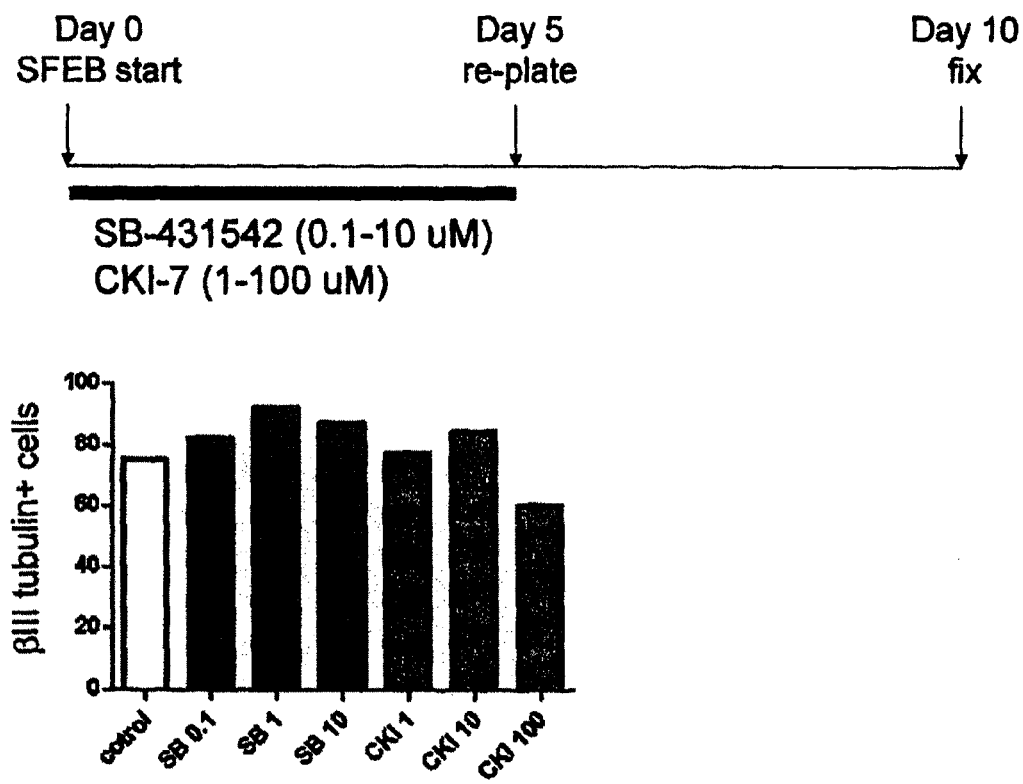
FIG. 10 Induction of differentiation of mouse ES cells into neural cells (βII tubulin-positive cells) by SB-431542 (SB) or CKI-7 (CKI). Drug concentration: μM.

As a result, with the addition of SB-431542 or CKI-7, the number of βII tubulin-positive cells increased (FIG. 10). This shows that SB-431542 and CKI-7 are each capable of enhancing differentiation of neuronal cells from ES cells. Furthermore, when both SB-431542 (5 μM) and CKI-7 (3 μM) were added to the medium, most (93.0±1.9%) cells became βII tubulin-positive. This suggests that combination of SB-431542 and CKI-7 synergistically accentuates the differentiation of neural cells from ES cells.

Example 4

Mouse ES cells were cultured under SFEB conditions in the presence of aSB-431542 (5 μM) and CKI-7 (3 μM); or SB-431542 (5 μM) and D4476 (3 μM). Three days after the start of the culture, the medium was replaced with a fresh differentiation medium containing 5% FCS. Four to 5 days after the start of the culture, Activin-A (R & D Systems, 10 ng/ml) was added to the medium. Five days after the start of the culture, the cells were recovered and re-suspended in a fresh differentiation medium, and, to produce re-aggregated pellets, the suspension was centrifuged at 800 g for 10 minutes. After cultivation at 37° C. for 1 hour, three to five re-aggregated pellets per $cm^2$ were replated onto a poly-D-lysine/laminin/fibronectin-coated culture slide, along with a differentiation medium. After 3 days of culture, in the same manner as Example 1, Rx/Pax6-positive cells were counted by immunohistological staining and FACS. The other experimental conditions were the same as those for Example 1.

As a result of immunohistological staining, even when SB-431542 and CKI-7 were used, $Rx^+$ $Pax6^+$ cells emerged as with DLFA. This showed that even when using SB-431542 and CKI-7 in place of Lefty-A and Dkk1, retinal progenitor cells were induced from ES cells. Results of FACS analysis showed that when ES cells were cultured using SB-431542 and CKI-7; or SB-431542 and D4476, 0.83% and 0.7% of the cells were Rx-positive, respectively. This result showed that even by combination use of SB-431542 and CKI-7, or by combination of SB-431542 and D4476, differentiation from ES cells to retinal progenitor cells is induced.

Example 5

Using SB-431542 (5 μM) and CKI-7 (3 μM) in place of Lefty-A and Dkk1, in the same manner as Example 2, the differentiation of human ES cells into RPE cells was investigated. As a result, as with the use of Lefty-A and Dkk1, pigment-positive colonies emerged 60 days after the start of the cultivation (FIG. 11). This result showed that even by combination of SB-431542 and CKI-7, differentiation from human ES cells to RPE cells is induced.

REFERENCE DOCUMENTS A

1. Haruta, M. et al. Induction of photoreceptor-specific phenotypes in adult mammalian iris tissue. Nat. Neurosci. 4, 1163-1164 (2001).
2. Sun, G. et al. Retinal stem/progenitor properties of iris pigment epithelial cells. Dev. Biol. 289, 243-252 (2006).
3. Tropepe, V. et al. Retinal stem cells in the adult mammalian eye. Science 287, 2032-2036 (2000).
4. Zhao, X., Liu, J. & Ahmad, I. Differentiation of embryonic stem cells into retinal neurons. Biochem. Biophys. Res. Commun. 297, 177-184 (2002).
5. Hirano, M. et al. Generation of structures formed by lens and retinal cells differentiating from embryonic stem cells. Dev. Dyn. 228, 664-671 (2003).
6. Ikeda, H. et al. Generation of Rx+/Pax6+ neural retinal precursors from embryonic stem cells. Proc. Natl. Acad. Sci. USA 102, 11331-11336 (2005).
7. Watanabe, K. et al. Directed differentiation of telencephalic precursors from embryonic stem cells. Nat. Neurosci. 8, 288-296 (2005).
8. Mathers, P. H., Grinberg, A., Mahon, K. A. & Jamrich, M. The Rx homeobox gene is essential for vertebrate eye development. Nature 387, 603-607 (1997).
9. Furukawa, T., Kozak, C. A. & Cepko, C. L. rax, a novel paired-type homeobox gene, shows expression in the anterior neural fold and developing retina. Proc. Natl. Acad. Sci. USA 94, 3088-3093 (1997).
10. Furukawa, T., Morrow, E. M. & Cepko, C. L. Crx, a novel otx-like homeobox gene, shows photoreceptor-specific expression and regulates photoreceptor differentiation. Cell 91, 531-541 (1997).
11. Chen, S. et al. Crx, a novel Otx-like paired-homeodomain protein, binds to and transactivates photoreceptor cell-specific genes. Neuron 19, 1017-1030 (1997).
12. Kubo, F., Takeichi, M. & Nakagawa, S. Wnt2b inhibits differentiation of retinal progenitor cells in the absence of Notch activity by downregulating the expression of proneural genes. Development 132, 2759-2770 (2005).
13. Jadhav, A. P., Mason, H. A. & Cepko, C. L. Notch 1 inhibits photoreceptor production in the developing mammalian retina. Development 133, 913-923 (2006).
14. Yaron, O. et al. Notch1 functions to suppress cone-photoreceptor fate specification in the developing mouse retina. Development 133, 1367-1378 (2006).
15. Dovey, H. F. et al. Functional gamma-secretase inhibitors reduce beta-amyloid peptide levels in brain. J. Neurochem. 76, 173-181 (2001).
16. Geling, A. et al. A γ-secretase inhibitor blocks Notch signaling in vivo and causes a severe neurogenic phenotype in zebrafish. EMBO Rep. 3, 688-694 (2002).
17. Shi, Y. Mechanisms of caspase activation and inhibition during apoptosis. Mol. Cell. 9, 459-470 (2002).
18. Levine, E. M., Fuhrmann, S. & Reh, T. A. Soluble factors and the development of rod photoreceptors. Cell. Mol. Life. Sci. 57, 224-234 (2000).
19. McGinnis, J. F. et al. Unique retina cell phenotypes revealed by immunological analysis of recoverin expression in rat retina cells. J. Neurosci. Res. 55, 252-260 (1999).
20. Kawasaki, H. et al. Induction of midbrain dopaminergic neurons from ES cells by stromal cell-derived inducing activity. Neuron 28, 31-40 (2000).
21. Su, H. L. et al. Generation of cerebellar neuron precursors from embryonic stem cells. Dev. Biol. 290, 287-296 (2006).
22. Kaneta, M. et al. A role for Pref-1 and HES-1 in thymocyte development. J. Immunol. 164, 256-264 (2000).
23. Chen, L. & Al-Awqati, Q. Segmental expression of Notch and Hairy genes in nephrodevelopment. Am. J. Physiol. Renal Physiol. 288, F939-F952 (2005).
24. Mizuseki, K. et al. Generation of neural crest-derived peripheral neurons and floor plate cells from mouse and primate embryonic stem cells. Proc. Natl. Acad. Sci. USA100, 5828-5833 (2003).

REFERENCE DOCUMENTS B

1. Rattner, A. & Nathans, J. Macular degeneration: recent advances and therapeutic opportunities. Nat Rev Neurosci. 7, 860-872 (2006).
2. Kaplan, H. J., Tezel, T. H., Berger, A. S., Wolf, M. L. & Del Priore, L. V. Human photoreceptor transplantation in retinitis pigmentosa. A safety study. Arch Opthalmol. 115, 1168-7112 (1997).
3. Takahashi, M., Palmer, T. D., Takahashi, J. & Gage, F. H. Widespread integration and survival of adult-derived neural progenitor cells in the developing optic retina. Mol Cell Neurosci. 12, 340-348 (1998).
4. Radtke, N. D., Aramant, R. B, Seiler, M. J., Petry, H. M. & Pidwell, D. Vision change after sheet transplant of fetal retina with retinal pigment epithelium to a patient with retinitis pigmentosa. Arch Opthalmol. 122, 1159-1165 (2004).
5. MacLaren, R. E. et al. Retinal repair by transplantation of photoreceptor precursors. Nature in press
6. Thomson. J. A. et al. Embryonic stem cell lines derived from human blastocysts. Science. 282, 1145-1147 (1998).
7. Zhao, X., Liu, J. & Ahmad, I. Differentiation of embryonic stem cells into retinal neurons. Biochem. Biophys. Res. Commun. 297, 177-184 (2002).
8. Hirano, M. et al. Generation of structures formed by lens and retinal cells differentiating from embryonic stem cells. Dev. Dyn. 228, 664-671 (2003).
9. Ikeda, H. et al. Generation of Rx+/Pax6+ neural retinal precursors from embryonic stem cells. Proc. Natl. Acad. Sci. USA 102, 11331-11336 (2005).
10. Lamba, D. A., Karl, M. O., Ware, C. B. & Reh, T. A. Efficient generation of retinal progenitor cells from human embryonic stem cells. Proc Natl Acad Sci USA. 103, 12769-12774 (2006).
11. Watanabe, K. et al. Directed differentiation of telencephalic precursors from embryonic stem cells. Nat. Neurosci. 8, 288-296 (2005).
12. Mathers, P. H., Grinberg, A., Mahon, K. A. & Jamrich, M. The Rx homeobox gene is essential for vertebrate eye development. Nature 387, 603-607 (1997).
13. Furukawa, T., Kozak, C. A. & Cepko, C. L. rax, a novel paired-type homeobox gene, shows expression in the anterior neural fold and developing retina. Proc. Natl. Acad. Sci. USA 94, 3088-3093 (1997).
14. Bora, N., Conway, S. J., Liang, H. & Smith, S. B. Transient overexpression of the Microphthalmia gene in the eyes of Microphthalmia vitiligo mutant mice. Dev Dyn. 213, 283-292 (1998).
15. Nguyen M. & Arnheiter H. Signaling and transcriptional regulation in early mammalian eye development: a link between FGF and MITF. Development 127, 3581-3591 (2000).
16. Baumer, N. et al. Retinal pigmented epithelium determination requires the redundant activities of Pax2 and Pax6. Development 130, 2903-2915 (2003).
17. Burke, J. M. in The Retinal Pigment Epithelium (eds. Marmor, M. F. & Wolfensberger, T. J.) 86-102 (Oxford Univ. Press, New York, 1998).
18. Furukawa, T., Morrow, E. M. & Cepko, C. L. Crx, a novel otx-like homeobox gene, shows photoreceptor-specific expression and regulates photoreceptor differentiation. Cell 91, 531-541 (1997).
19. Chen, S. et al. Crx, a novel Otx-like paired-homeodomain protein, binds to and transactivates photoreceptor cell-specific genes. Neuron 19, 1017-1030 (1997).
20. Hyatt G. A. & Dowling J. E. Invest Opthalmol Vis Sci. 38, 1471-1475 (1997).
21. Levine, E. M., Fuhrmann, S. & Reh, T. A. Soluble factors and the development of rod photoreceptors. Cell. Mol. Life. Sci. 57, 224-234 (2000).
22. Altshuler, D. & Cepko, C. A temporally regulated, diffusible activity is required for rod photoreceptor development in vitro. Development. 114, 947-957 (1992).
23. Young, T. L. & Cepko, C. L. A role for ligand-gated ion channels in rod photoreceptor development. Neuron. 41, 867-879 (2004).
24. McGinnis, J. F. et al. Unique retina cell phenotypes revealed by immunological analysis of recoverin expression in rat retina cells. J. Neurosci. Res. 55, 252-260 (1999).
25. Boulton, M. in The Retinal Pigment Epithelium (eds. Marmor, M. F. & Wolfensberger, T. J.) 68-85 (Oxford Univ. Press, New York, 1998).
26. Haruta, M. et al. In vitro and in vivo characterization of pigment epithelial cells differentiated from primate embryonic stem cells. Invest. Opthalmol. Vis. Sci. 45, 1020-1025 (2004).
27. Martin, M. J., Muotri, A., Gage. F. & Varki, A. Human embryonic stem cells express an immunogenic nonhuman sialic acid. Nat. Med. 11, 228-232 (2005).
28. Suemori, H. et al. Establishment of embryonic stem cell lines from cynomolgus monkey blastocysts produced by IVF or ICSI. Dev Dyn. 222, 273-279 (2001).
29. Kawasaki, H. et al. Generation of dopaminergic neurons and pigmented epithelia from primate ES cells by stromal cell-derived inducing activity. Proc. Natl. Acad. Sci. USA 99, 1580-1585 (2002).
30. Nichols, J. et al. Formation of pluripotent stem cells in the mammalian embryo depends on the POU transcription factor Oct4. Cell. 95, 379-391 (1998).
31. Mitsui, K. et al. The homeoprotein Nanog is required for maintenance of pluripotency in mouse epiblast and ES cells. Cell. 113, 631-642 (2003).
32. Chambers, I. et al. Functional expression cloning of Nanog, a pluripotency sustaining factor in embryonic stem cells. Cell. 113, 643-655 (2003).
33. Ueno, M. et al. Neural conversion of ES cells by an inductive activity on human amniotic membrane matrix. Proc. Natl. Acad. Sci. USA. 103, 9554-9559 (2006).
34. Mizuseki, K. et al. Generation of neural crest-derived peripheral neurons and floor plate cells from mouse and primate embryonic stem cells. Proc. Natl. Acad. Sci. USA100, 5828-5833 (2003).

INDUSTRIAL APPLICABILITY

Using a method of the present invention, retinal progenitor cells or photoreceptors can be efficiently generated from an ES cell without co-culture with retinal tissue. In particular, a method of the present invention is advantageous in that retinal progenitor cells or photoreceptors can be efficiently produced from primate ES cells under the defined culture conditions.

The present invention is expected to remarkably promote the development of a transplantation therapy for retinal diseases based on human ES cells.

This application is based on a patent application No. 2007-009617 filed in Japan (filing date: Jan. 18, 2007), the contents of which are incorporated in full herein by this reference.

What is claimed is:

1. A method of producing photoreceptor precursors, comprising
    (a) culturing mammalian embryonic stem cells as suspended aggregates in a medium such that the ES cells differentiate into retinal progenitor cells indicated by the expression of a retinal progenitor cell maker selected from the group of Pax6, Rx and Mitf;
    (b) culturing the retinal progenitor cells differentiated from the embryonic stem cells under adhesive conditions in the presence of a gamma secretase inhibitor to produce photoreceptor precursors indicated by the expression of the photoreceptor precursor marker selected from the group Crx and rhodopsin;
    (c) isolating photoreceptor precursors from the culture.

2. The method of claim 1, wherein the gamma secretase inhibitor is N—[N-(3,5-difluorophenacetyl)-L-alanyl]-S-phenylglycine t-butyl ester (DAPT).

3. A method of producing cone photoreceptors, comprising
    (a) culturing mammalian embryonic stem cells as suspended aggregates in a medium such that the ES cells differentiate into retinal progenitor cells indicated by the expression of a retinal progenitor cell maker selected from the group of Pax6, Rx and Mitf;

(b) culturing the retinal progenitor cells differentiated from the embryonic stem cells under adhesive conditions in the presence of a gamma secretase inhibitor to produce photoreceptor precursors indicated by the expression of the photoreceptor precursor marker selected from the group Crx and rhodopsin;

(c) culturing the photoreceptor precursor cells under adhesive conditions in a medium comprising a gamma secretase inhibitor and one of aFGF, bFGF, taurine, Shh or RA to produce cone photoreceptors indicated by the expression of a photoreceptor maker selected from the group rhodopsin, red/green opsin, blue opsin and Recoverin; and (d) isolating cone photoreceptors from the culture.

4. The method of claim 3, wherein the gamma secretase inhibitor is N—[N-(3,5-difluorophenacetyl)-L-alanyl]-S-phenylglycine t-butyl ester (DAPT).

5. The method of claim 1, wherein the culturing of the embryonic stem cells as suspended aggregates is performed in a serum-free medium containing at least one inhibitor selected from the group consisting of a Nodal signal inhibitor and a Wnt signal inhibitor.

6. The method of claim 3, wherein the culturing of the embryonic stem cells as suspended aggregates is performed in a serum-free medium containing at least one inhibitor selected from the group consisting of a Nodal signal inhibitor and a Wnt signal inhibitor.

7. The method of claim 6, wherein the Nodal signal inhibitor is Lefty-A, Lefty-B, Lefty-1, Lefty-2, soluble Nodal receptor, Nodal antibody, Nodal receptor inhibitor, or SB-431242.

8. The method of claim 7, wherein the Nodal signal inhibitor is Lefty-A or SB-431542.

9. The method of claim 6, wherein the Wnt signal inhibitor is Dkk1, Cerberus protein, Wnt receptor inhibitor, soluble Wnt receptor, Wnt antibody, casein kinase inhibitor, dominant negative Wnt protein, N-(2-aminoethyl)-5-chloro-isoquinoline-8-sulfonamide (CKI-7), or 4-{4-(2,3-dihydrobenzo[1,4]dioxyn-6-yl)-5-pyridin-2-yl-1H-imidazol-2-yl}benzamide (D4476).

10. The method of claim 9, wherein the Wnt signal inhibitor is Dkk1, CKI-7, or D4476.

11. The method of claim 6, wherein the Nodal signal inhibitor is Lefty-A, Lefty-B, Lefty-1, Lefty-2, soluble Nodal receptor, Nodal antibody, Nodal receptor inhibitor, or SB-431242, and wherein the Wnt signal inhibitor is Dkk1, Cerberus protein, Wnt receptor inhibitor, soluble Wnt receptor, Wnt antibody, casein kinase inhibitor, dominant negative Wnt protein, N-(2-aminoethyl)-5-chloro-isoquinoline-8-sulfonamide (CKI-7), or 4-{442,3-dihydrobenzo[1,4]dioxyn-6-yl)-5-pyridin-2-yl-1H-imidazol-2-yl}benzamide (D4476).

12. The method of claim 11, wherein the mammalian embryonic stem cells are human embryonic stem cells.

13. The method of claim 4, wherein the culturing of the embryonic stem cells as suspended aggregates is performed in a serum-free medium containing at least one inhibitor selected from the group consisting of a Nodal signal inhibitor and a Wnt signal inhibitor.

14. The method of claim 13, wherein the Nodal signal inhibitor is Lefty-A, Lefty-B, Lefty-1, Lefty-2, soluble Nodal receptor, Nodal antibody, Nodal receptor inhibitor, or SB-431242, and wherein the Wnt signal inhibitor is Dkk1, Cerberus protein, Wnt receptor inhibitor, soluble Wnt receptor, Wnt antibody, casein kinase inhibitor, dominant negative Wnt protein, N-(2-aminoethyl)-5-chloro-isoquinoline-8-sulfonamide (CKI-7), or 4-{4-(2,3-dihydrobenzo[1,4]dioxyn-6-yl)-5-pyridin-2-yl-1H-imidazol-2-yl}benzamide (D4476).

15. The method of claim 14, wherein the Nodal signal inhibitor is Lefty-A or SB-431542, and wherein the Wnt signal inhibitor is Dkk1, CKI-7, or D4476.

16. The method of claim 3, wherein the mammalian embryonic stem cells are human embryonic stem cells.

17. The method of claim 5, wherein the Nodal signal inhibitor is Lefty-A, Lefty-B, Lefty-1, Lefty-2, soluble Nodal receptor, Nodal antibody, Nodal receptor inhibitor, or SB-431242.

18. The method of claim 17, wherein the Nodal signal inhibitor is Lefty-A or SB-431542.

19. The method of claim 5, wherein the Wnt signal inhibitor is Dkk1, Cerberus protein, Wnt receptor inhibitor, soluble Wnt receptor, Wnt antibody, casein kinase inhibitor, dominant negative Wnt protein, N-(2-aminoethyl)-5-chloro-isoquinoline-8-sulfonamide (CKI-7), or 4-{4-(2,3-dihydrobenzo[1,4]dioxyn-6-yl)-5-pyridin-2-yl-1H-imidazol-2-yl}benzamide (D4476).

20. The method of claim 19, wherein the Wnt signal inhibitor is Dkk1, CKI-7, or D4476.

21. The method of claim 5, wherein the Nodal signal inhibitor is Lefty-A, Lefty-B, Lefty-1, Lefty-2, soluble Nodal receptor, Nodal antibody, Nodal receptor inhibitor, or SB-431242, and wherein the Wnt signal inhibitor is Dkk1, Cerberus protein, Wnt receptor inhibitor, soluble Wnt receptor, Wnt antibody, casein kinase inhibitor, dominant negative Wnt protein, N-(2-aminoethyl)-5-chloro-isoquinoline-8-sulfonamide (CKI-7), or 4-{4-(2,3-dihydrobenzo[1,4]dioxyn-6-yl)-5-pyridin-2-yl-1H-imidazol-2-yl}benzamide (D4476).

22. The method of claim 21, wherein the mammalian embryonic stem cells are human embryonic stem cells.

23. The method of claim 2, wherein the culturing of the embryonic stem cells as suspended aggregates is performed in a serum-free medium containing at least one inhibitor selected from the group consisting of a Nodal signal inhibitor and a Wnt signal inhibitor.

24. The method of claim 23, wherein the Nodal signal inhibitor is Lefty-A, Lefty-B, Lefty-1, Lefty-2, soluble Nodal receptor, Nodal antibody, Nodal receptor inhibitor, or SB-431242, and wherein the Wnt signal inhibitor is Dkk1, Cerberus protein, Wnt receptor inhibitor, soluble Wnt receptor, Wnt antibody, casein kinase inhibitor, dominant negative Wnt protein, N-(2-aminoethyl)-5-chloro-isoquinoline-8-sulfonamide (CKI-7), or 4-{4-(2,3-dihydrobenzo[1,4]dioxyn-6-yl)-5-pyridin-2-yl-1H-imidazol-1-yl}benzamide (D4476).

25. The method of claim 24, wherein the Nodal signal inhibitor is Lefty-A or SB-431542, and wherein the Wnt signal inhibitor is Dkk1, CKI-7, or D4476.

26. The method of claim 1, wherein the mammalian embryonic stem cells are human embryonic stem cells.

* * * * *

SEQUENCE LISTING

<160> NUMBER OF SEQ ID NOS: 58

<210> SEQ ID NO 1
<211> LENGTH: 21
<212> TYPE: DNA
<213> ORGANISM: Artificial
<220> FEATURE:
<223> OTHER INFORMATION: primer for Notch 1

<400> SEQUENCE: 1
tgcctgtgca caccattctg c                                              21

<210> SEQ ID NO 2
<211> LENGTH: 21
<212> TYPE: DNA
<213> ORGANISM: Artificial
<220> FEATURE:
<223> OTHER INFORMATION: primer for Notch 1

<400> SEQUENCE: 2
caatcagaga tgttggaatg c                                              21

<210> SEQ ID NO 3
<211> LENGTH: 20
<212> TYPE: DNA
<213> ORGANISM: Artificial
<220> FEATURE:
<223> OTHER INFORMATION: primer for Notch 2

<400> SEQUENCE: 3
atgcaccatg acatcgttcg                                                20

<210> SEQ ID NO 4
<211> LENGTH: 21
<212> TYPE: DNA
<213> ORGANISM: Artificial
<220> FEATURE:
<223> OTHER INFORMATION: primer for Notch 2

<400> SEQUENCE: 4
gatagagtca ctgagctctc g                                              21

<210> SEQ ID NO 5
<211> LENGTH: 22
<212> TYPE: DNA
<213> ORGANISM: Artificial
<220> FEATURE:
<223> OTHER INFORMATION: primer for Notch 3

<400> SEQUENCE: 5
ttggtctgct caatcctgta gc                                             22

<210> SEQ ID NO 6
<211> LENGTH: 21
<212> TYPE: DNA
<213> ORGANISM: Artificial
<220> FEATURE:
<223> OTHER INFORMATION: primer for Notch 3

<400> SEQUENCE: 6
tggcattggt agcagttgct g                                              21

<210> SEQ ID NO 7
<211> LENGTH: 21
<212> TYPE: DNA
<213> ORGANISM: Artificial

```
<220> FEATURE:
<223> OTHER INFORMATION: primer for Notch 4

<400> SEQUENCE: 7
aagcgacacg tacgagtctg g                                      21

<210> SEQ ID NO 8
<211> LENGTH: 21
<212> TYPE: DNA
<213> ORGANISM: Artificial
<220> FEATURE:
<223> OTHER INFORMATION: primer for Notch 4

<400> SEQUENCE: 8
atagttgcca gctacttgtg g                                      21

<210> SEQ ID NO 9
<211> LENGTH: 19
<212> TYPE: DNA
<213> ORGANISM: Artificial
<220> FEATURE:
<223> OTHER INFORMATION: primer for Hes 1

<400> SEQUENCE: 9
tctacaccag caacagtgg                                         19

<210> SEQ ID NO 10
<211> LENGTH: 20
<212> TYPE: DNA
<213> ORGANISM: Artificial
<220> FEATURE:
<223> OTHER INFORMATION: primer for Hes 1

<400> SEQUENCE: 10
tcaaacatct ttggcatcac                                        20

<210> SEQ ID NO 11
<211> LENGTH: 21
<212> TYPE: DNA
<213> ORGANISM: Artificial
<220> FEATURE:
<223> OTHER INFORMATION: primer for Hes 5

<400> SEQUENCE: 11
aagtgacttc tgcgaagttc c                                      21

<210> SEQ ID NO 12
<211> LENGTH: 21
<212> TYPE: DNA
<213> ORGANISM: Artificial
<220> FEATURE:
<223> OTHER INFORMATION: primer for Hes 5

<400> SEQUENCE: 12
aaggccatgt ggaccttgag g                                      21

<210> SEQ ID NO 13
<211> LENGTH: 23
<212> TYPE: DNA
<213> ORGANISM: Artificial
<220> FEATURE:
<223> OTHER INFORMATION: primer for Hey 1

<400> SEQUENCE: 13
tcgagaagcg ccgacgagac cga                                    23
```

<210> SEQ ID NO 14
<211> LENGTH: 26
<212> TYPE: DNA
<213> ORGANISM: Artificial
<220> FEATURE:
<223> OTHER INFORMATION: primer for Hey 1

<400> SEQUENCE: 14
cagcagaggg tgtgcgatgt gtgggt                    26

<210> SEQ ID NO 15
<211> LENGTH: 20
<212> TYPE: DNA
<213> ORGANISM: Artificial
<220> FEATURE:
<223> OTHER INFORMATION: primer for gnat 1

<400> SEQUENCE: 15
gagcttaaca tgcgacgtga                           20

<210> SEQ ID NO 16
<211> LENGTH: 20
<212> TYPE: DNA
<213> ORGANISM: Artificial
<220> FEATURE:
<223> OTHER INFORMATION: primer for gnat 1

<400> SEQUENCE: 16
gctgctgtag gtccaagagg                           20

<210> SEQ ID NO 17
<211> LENGTH: 20
<212> TYPE: DNA
<213> ORGANISM: Artificial
<220> FEATURE:
<223> OTHER INFORMATION: primer for pde6b

<400> SEQUENCE: 17
catgaatggc aaagatgtcg                           20

<210> SEQ ID NO 18
<211> LENGTH: 20
<212> TYPE: DNA
<213> ORGANISM: Artificial
<220> FEATURE:
<223> OTHER INFORMATION: primer for pde6b

<400> SEQUENCE: 18
gtgttcgtgg gcctgagtat                           20

<210> SEQ ID NO 19
<211> LENGTH: 20
<212> TYPE: DNA
<213> ORGANISM: Artificial
<220> FEATURE:
<223> OTHER INFORMATION: primer for pde6c

<400> SEQUENCE: 19
gaggtccttg ctgtggtcat                           20

<210> SEQ ID NO 20
<211> LENGTH: 20
<212> TYPE: DNA
<213> ORGANISM: Artificial
<220> FEATURE:
<223> OTHER INFORMATION: primer for pde6c

```
<400> SEQUENCE: 20
ccttgtgaaa ctgtcgctca                                          20

<210> SEQ ID NO 21
<211> LENGTH: 20
<212> TYPE: DNA
<213> ORGANISM: Artificial
<220> FEATURE:
<223> OTHER INFORMATION: primer for cnga1

<400> SEQUENCE: 21
gagcaaggcc gatgataaaa                                          20

<210> SEQ ID NO 22
<211> LENGTH: 20
<212> TYPE: DNA
<213> ORGANISM: Artificial
<220> FEATURE:
<223> OTHER INFORMATION: primer for cnga1

<400> SEQUENCE: 22
tcactagcag cccttgttcc                                          20

<210> SEQ ID NO 23
<211> LENGTH: 20
<212> TYPE: DNA
<213> ORGANISM: Artificial
<220> FEATURE:
<223> OTHER INFORMATION: primer for sag

<400> SEQUENCE: 23
gtcctcaccc aactccaaga                                          20

<210> SEQ ID NO 24
<211> LENGTH: 20
<212> TYPE: DNA
<213> ORGANISM: Artificial
<220> FEATURE:
<223> OTHER INFORMATION: primer for sag

<400> SEQUENCE: 24
gttgttggtc acggtcacag                                          20

<210> SEQ ID NO 25
<211> LENGTH: 20
<212> TYPE: DNA
<213> ORGANISM: Artificial
<220> FEATURE:
<223> OTHER INFORMATION: primer for arr3

<400> SEQUENCE: 25
gtccttgttg accccgagta                                          20

<210> SEQ ID NO 26
<211> LENGTH: 20
<212> TYPE: DNA
<213> ORGANISM: Artificial
<220> FEATURE:
<223> OTHER INFORMATION: primer for arr3

<400> SEQUENCE: 26
ctgcactttc cgtacaacca                                          20

<210> SEQ ID NO 27
```

```
<211> LENGTH: 20
<212> TYPE: DNA
<213> ORGANISM: Artificial
<220> FEATURE:
<223> OTHER INFORMATION: primer for Grk1

<400> SEQUENCE: 27
ctgcatcaga gacgcattgt                                                   20

<210> SEQ ID NO 28
<211> LENGTH: 20
<212> TYPE: DNA
<213> ORGANISM: Artificial
<220> FEATURE:
<223> OTHER INFORMATION: primer for Grk1

<400> SEQUENCE: 28
tctccaacag ctgctcacag                                                   20

<210> SEQ ID NO 29
<211> LENGTH: 20
<212> TYPE: DNA
<213> ORGANISM: Artificial
<220> FEATURE:
<223> OTHER INFORMATION: primer for pdc

<400> SEQUENCE: 29
cacacaggac ccaaaggagt                                                   20

<210> SEQ ID NO 30
<211> LENGTH: 20
<212> TYPE: DNA
<213> ORGANISM: Artificial
<220> FEATURE:
<223> OTHER INFORMATION: primer for pdc

<400> SEQUENCE: 30
tctgctcctt ctcgatggtt                                                   20

<210> SEQ ID NO 31
<211> LENGTH: 20
<212> TYPE: DNA
<213> ORGANISM: Artificial
<220> FEATURE:
<223> OTHER INFORMATION: primer for rdh12

<400> SEQUENCE: 31
ggccaatctg ctcttcactc                                                   20

<210> SEQ ID NO 32
<211> LENGTH: 20
<212> TYPE: DNA
<213> ORGANISM: Artificial
<220> FEATURE:
<223> OTHER INFORMATION: primer for rdh12

<400> SEQUENCE: 32
tgaaaaggct ctggtcttcg                                                   20

<210> SEQ ID NO 33
<211> LENGTH: 20
<212> TYPE: DNA
<213> ORGANISM: Artificial
<220> FEATURE:
<223> OTHER INFORMATION: primer for rbp3

<400> SEQUENCE: 33
```

```
ttccctcccc agaagtcttt                                              20

<210> SEQ ID NO 34
<211> LENGTH: 20
<212> TYPE: DNA
<213> ORGANISM: Artificial
<220> FEATURE:
<223> OTHER INFORMATION: primer for rbp3

<400> SEQUENCE: 34
ggatggctac gctcttcttg                                              20

<210> SEQ ID NO 35
<211> LENGTH: 20
<212> TYPE: DNA
<213> ORGANISM: Artificial
<220> FEATURE:
<223> OTHER INFORMATION: primer for rp1h

<400> SEQUENCE: 35
cgaagccttt ctgcagtacc                                              20

<210> SEQ ID NO 36
<211> LENGTH: 20
<212> TYPE: DNA
<213> ORGANISM: Artificial
<220> FEATURE:
<223> OTHER INFORMATION: primer for rp1h

<400> SEQUENCE: 36
agggaatcag tctggggtct                                              20

<210> SEQ ID NO 37
<211> LENGTH: 20
<212> TYPE: DNA
<213> ORGANISM: Artificial
<220> FEATURE:
<223> OTHER INFORMATION: primer for rpgrip1

<400> SEQUENCE: 37
cagactaccg acagcgatga                                              20

<210> SEQ ID NO 38
<211> LENGTH: 20
<212> TYPE: DNA
<213> ORGANISM: Artificial
<220> FEATURE:
<223> OTHER INFORMATION: primer for rpgrip1

<400> SEQUENCE: 38
ttggtttcct cagggacatc                                              20

<210> SEQ ID NO 39
<211> LENGTH: 20
<212> TYPE: DNA
<213> ORGANISM: Artificial
<220> FEATURE:
<223> OTHER INFORMATION: primer for GNAT1

<400> SEQUENCE: 39
catcgagacg cagttctcct                                              20

<210> SEQ ID NO 40
<211> LENGTH: 20
<212> TYPE: DNA
```

```
<213> ORGANISM: Artificial
<220> FEATURE:
<223> OTHER INFORMATION: primer for GNAT1

<400> SEQUENCE: 40
agtagcggtg gttgcagatg                                            20

<210> SEQ ID NO 41
<211> LENGTH: 20
<212> TYPE: DNA
<213> ORGANISM: Artificial
<220> FEATURE:
<223> OTHER INFORMATION: primer for PDC

<400> SEQUENCE: 41
tcaaaggaac gagtcagcag                                            20

<210> SEQ ID NO 42
<211> LENGTH: 20
<212> TYPE: DNA
<213> ORGANISM: Artificial
<220> FEATURE:
<223> OTHER INFORMATION: primer for PDC

<400> SEQUENCE: 42
ctgctgcaag gcatgttaaa                                            20

<210> SEQ ID NO 43
<211> LENGTH: 20
<212> TYPE: DNA
<213> ORGANISM: Artificial
<220> FEATURE:
<223> OTHER INFORMATION: primer for PDE6b

<400> SEQUENCE: 43
cagtgatgaa caccgacacc                                            20

<210> SEQ ID NO 44
<211> LENGTH: 20
<212> TYPE: DNA
<213> ORGANISM: Artificial
<220> FEATURE:
<223> OTHER INFORMATION: primer for PDE6b

<400> SEQUENCE: 44
atttgaccag gtccagttcg                                            20

<210> SEQ ID NO 45
<211> LENGTH: 20
<212> TYPE: DNA
<213> ORGANISM: Artificial
<220> FEATURE:
<223> OTHER INFORMATION: primer for PDE6c

<400> SEQUENCE: 45
ctgaggtggc ctctaggttg                                            20

<210> SEQ ID NO 46
<211> LENGTH: 21
<212> TYPE: DNA
<213> ORGANISM: Artificial
<220> FEATURE:
<223> OTHER INFORMATION: primer for PDE6c

<400> SEQUENCE: 46
gctggtgtga tgaagcctta g                                          21
```

<210> SEQ ID NO 47
<211> LENGTH: 20
<212> TYPE: DNA
<213> ORGANISM: Artificial
<220> FEATURE:
<223> OTHER INFORMATION: primer for CNGA1

<400> SEQUENCE: 47
gatccctcgg gaaacacata                                                  20

<210> SEQ ID NO 48
<211> LENGTH: 22
<212> TYPE: DNA
<213> ORGANISM: Artificial
<220> FEATURE:
<223> OTHER INFORMATION: primer for CNGA1

<400> SEQUENCE: 48
cgagagaacc gtaacaacct gg                                               22

<210> SEQ ID NO 49
<211> LENGTH: 20
<212> TYPE: DNA
<213> ORGANISM: Artificial
<220> FEATURE:
<223> OTHER INFORMATION: primer for GRK1

<400> SEQUENCE: 49
ggactggttc ctggacttca                                                  20

<210> SEQ ID NO 50
<211> LENGTH: 20
<212> TYPE: DNA
<213> ORGANISM: Artificial
<220> FEATURE:
<223> OTHER INFORMATION: primer for GRK1

<400> SEQUENCE: 50
aagccagggt tctcctcatt                                                  20

<210> SEQ ID NO 51
<211> LENGTH: 20
<212> TYPE: DNA
<213> ORGANISM: Artificial
<220> FEATURE:
<223> OTHER INFORMATION: primer for SAG

<400> SEQUENCE: 51
ggtgttgtcc tggttgatcc                                                  20

<210> SEQ ID NO 52
<211> LENGTH: 20
<212> TYPE: DNA
<213> ORGANISM: Artificial
<220> FEATURE:
<223> OTHER INFORMATION: primer for SAG

<400> SEQUENCE: 52
tcagcgtctt ggtcaaagtg                                                  20

<210> SEQ ID NO 53
<211> LENGTH: 20
<212> TYPE: DNA
<213> ORGANISM: Artificial
<220> FEATURE:

```
<223> OTHER INFORMATION: primer for ARR3

<400> SEQUENCE: 53
ggtgttgtcc tggttgatcc                                          20

<210> SEQ ID NO 54
<211> LENGTH: 20
<212> TYPE: DNA
<213> ORGANISM: Artificial
<220> FEATURE:
<223> OTHER INFORMATION: primer for ARR3

<400> SEQUENCE: 54
gtcacagaac agggcaggtt                                          20

<210> SEQ ID NO 55
<211> LENGTH: 20
<212> TYPE: DNA
<213> ORGANISM: Artificial
<220> FEATURE:
<223> OTHER INFORMATION: primer for RDH12

<400> SEQUENCE: 55
cttctccccc tttgtcaaga                                          20

<210> SEQ ID NO 56
<211> LENGTH: 20
<212> TYPE: DNA
<213> ORGANISM: Artificial
<220> FEATURE:
<223> OTHER INFORMATION: primer for RDH12

<400> SEQUENCE: 56
ctttagggtt ggccttctcc                                          20

<210> SEQ ID NO 57
<211> LENGTH: 20
<212> TYPE: DNA
<213> ORGANISM: Artificial
<220> FEATURE:
<223> OTHER INFORMATION: primer for GAPDH

<400> SEQUENCE: 57
gcctctaggt tgctggatgt                                          20

<210> SEQ ID NO 58
<211> LENGTH: 21
<212> TYPE: DNA
<213> ORGANISM: Artificial
<220> FEATURE:
<223> OTHER INFORMATION: primer for GAPDH

<400> SEQUENCE: 58
gctggtgtga tgaagcctta g                                        21
```